(12) United States Patent
Cotton et al.

(10) Patent No.: US 8,545,866 B2
(45) Date of Patent: Oct. 1, 2013

(54) BIOABSORBABLE POLYMERS

(75) Inventors: Nicholas John Cotton, Westborough, MA (US); Melissa Jane Egan, Plympton, MA (US)

(73) Assignee: Smith & Nephew, Inc., Andover, MA (US)

( * ) Notice: Subject to any disclaimer, the term of this patent is extended or adjusted under 35 U.S.C. 154(b) by 149 days.

(21) Appl. No.: 12/847,511

(22) Filed: Jul. 30, 2010

(65) Prior Publication Data

US 2010/0316591 A1 Dec. 16, 2010

Related U.S. Application Data

(63) Continuation-in-part of application No. 11/262,336, filed on Oct. 28, 2005, now abandoned.

(60) Provisional application No. 60/623,645, filed on Oct. 29, 2004.

(51) Int. Cl.
*A61F 2/00* (2006.01)

(52) U.S. Cl.
USPC .......................................................... 424/423

(58) Field of Classification Search
None
See application file for complete search history.

(56) References Cited

U.S. PATENT DOCUMENTS

| | | |
|---|---|---|
| 4,781,183 A | 11/1988 | Casey et al. |
| 4,834,752 A * | 5/1989 | Van Kampen ............. 623/13.14 |
| 5,019,093 A | 5/1991 | Kaplan et al. |
| 5,286,763 A | 2/1994 | Gernhart et al. |
| 5,433,751 A | 7/1995 | Christel et al. |
| 5,492,687 A | 2/1996 | Ruddy et al. |
| 5,679,723 A | 10/1997 | Cooper et al. |
| 5,681,873 A | 10/1997 | Norton et al. |
| 5,741,329 A | 4/1998 | Agrawal et al. |
| 5,817,328 A | 10/1998 | Gresser et al. |
| 6,027,742 A | 2/2000 | Lee et al. |
| 6,344,496 B1 | 2/2002 | Niederauer et al. |
| 6,486,232 B1 | 11/2002 | Wise et al. |
| 6,524,345 B1 | 2/2003 | Valimaa et al. |
| 6,599,516 B1 | 7/2003 | Knaack |
| 6,632,224 B2 * | 10/2003 | Cachia et al. ................. 606/304 |
| 6,685,706 B2 * | 2/2004 | Padget et al. ................. 606/309 |
| 6,689,166 B2 | 2/2004 | Laurencin et al. |
| 6,741,329 B2 | 5/2004 | Leenders et al. |
| 6,787,584 B2 | 9/2004 | Jia et al. |
| 6,867,247 B2 | 3/2005 | Williams et al. |

(Continued)

FOREIGN PATENT DOCUMENTS

| | | |
|---|---|---|
| CN | 1403166 | 3/2003 |
| CN | 1403167 | 3/2003 |

(Continued)

OTHER PUBLICATIONS

Anthanasiou, et al., Biomaterials 17:93-102, 1996.

(Continued)

*Primary Examiner* — Paul Dickinson
(74) *Attorney, Agent, or Firm* — JL Salazar Law Firm; David L. Fox

(57) ABSTRACT

Described herein are biocompatible compositions that contain a copolymer and a filler material. In particular, described herein are compositions that include a copolymer and a filler which may be a calcium salt. Also described herein are methods in which the compositions are used to attach soft tissue to bone.

24 Claims, 13 Drawing Sheets

| I. Material | II. Percent Mass Loss | | | |
|---|---|---|---|---|
| | 1 Day | 2 Day | 4 day | 5 day |
| PDLG (Chloroform) | 0 | 0 | 68 | 98 |
| PDLG (Raw) | 0 | 18 | 47 | 95 |
| PDLG + Calcium Carbonate | 0.6 | 1.1 | 9 | 36 |
| PDLG +Calcium Sulphate | 1.6 | 2 | | 85 |

(56) References Cited

U.S. PATENT DOCUMENTS

| | | | |
|---|---|---|---|
| 7,604,817 B2 * | 10/2009 | Yi et al. ................. 424/423 |
| 2002/0120348 A1 | 8/2002 | Melican et al. |
| 2003/0031698 A1 | 2/2003 | Roeder et al. |
| 2003/0055512 A1 | 3/2003 | Genin et al. |
| 2003/0129401 A1 | 7/2003 | Manfredi et al. |
| 2003/0232071 A1 | 12/2003 | Gower et al. |
| 2004/0002770 A1 | 1/2004 | King et al. |
| 2004/0247644 A1 * | 12/2004 | Bratt et al. ................. 424/426 |
| 2004/0260398 A1 * | 12/2004 | Kelman ................. 623/19.11 |
| 2006/0067973 A1 | 3/2006 | Schachter |
| 2006/0074422 A1 | 4/2006 | Story et al. |
| 2007/0191963 A1 | 8/2007 | Winterbottom |

FOREIGN PATENT DOCUMENTS

| | | |
|---|---|---|
| CN | 1586416 | 3/2005 |
| EP | 714666 | 6/1996 |
| EP | 1009448 | 6/2000 |
| EP | 1229858 | 8/2002 |
| FR | 2364644 | 4/1978 |
| JP | 2002210002 | 7/2002 |
| WO | WO 0018443 | 4/2000 |
| WO | 00/30552 | 6/2000 |
| WO | 01/66044 | 9/2001 |
| WO | WO 03024316 | 3/2003 |
| WO | WO 03030956 | 4/2003 |
| WO | 2005/018700 | 3/2005 |
| WO | 2005/061617 | 7/2005 |

OTHER PUBLICATIONS

Baker, et al., J. Biomed. Mat. Res. 46:573-581, 1999.
Besong, et al., J. Bone Joint Surg. 80-B:340-344, 1998.
Buchanan, et al., Biomaterials 20:823-837, 1999.
Costa, et al., Biomaterials 19:659-668, 1998.
Dillow, et al., Proc. Natl, Acad, Sci., USA 96:10344-10348, 1999.
Gogolewski, et al., Biomaterials, 17:523-528, 1996.
Gogolewski, et al., Biomaterials, 18:251-255, 1997.
Grana, Am. J. Sports Med. 22:344-351, 1994.
Kurtz, et al., J. Biomed. Mat. Res. 46:112-120, 1999.
Kurtz, et al., Biomaterials, 20:1659-1688, 1999.
Pascaud, et al., Biomaterials 18:727-735, 1997.
Rodeo, et al., Journal. Bone Joint Surg, 75-A:1795-1803, 1993.
Ratner, et al., Eds., Biomaterials Science: An Introduction to Materials in Medicine, Academic Press, pp. 415-420, 1996.
Sauer, et al., Biomaterials, 11:1929-1935, 1996.
Weiler, et al., Arthroscopy, 18:113-123, 2002.
Agrawal & Athanasion, "Techniques to control pH in vicinity of biodegrading PLA-PGA implants," 1. Biomed. Matter Res. 38: 105-114, 1997.
Schiller et al, Geometrically structured implants for cranial reconstruction made of biodegradable polyesters and calcium phosphate/calcium carbonate, Biomaterials, 2004, 25, 1239-1247.

* cited by examiner

| I. Material | II. Percent Mass Loss | | | |
|---|---|---|---|---|
| | 1 Day | 2 Day | 4 day | 5 day |
| PDLG (Chloroform) | 0 | 0 | 68 | 98 |
| PDLG (Raw) | 0 | 18 | 47 | 95 |
| PDLG + Calcium Carbonate | 0.6 | 1.1 | 9 | 36 |
| PDLG +Calcium Sulphate | 1.6 | 2 | | 85 |

Figure 2a. Molecular weight (Mw) during accelerated degradation

| Day | PDLG CHCl$_3$ processed | PDLG resin | PDLG + 40% CaCO$_3$ | PDLG + 40% CaSO$_4$ |
|---|---|---|---|---|
| 0 | 90195 | 132400 | 167550 | 164550 |
| 1 | 20910 | 21430 | 97310 | 65270 |
| 2 | 6945 | 3825 | 26680 | 13320 |
| 4 | 1366 | 2615 | 4527 | 1178 |

Figure 2b. Molecular weight (Mw) during accelerated degradation

Figure 3. Torsional strengths using pass / fail criteria
| Material | Standard Industry Torsional Test |
|---|---|
| PDLG | PASS |
| PLC 15 | PASS |
| PLC 35 | PASS |
| PLC 50 | FAIL |
Figure 4. Molecular weight (Mw) during real time degradation.
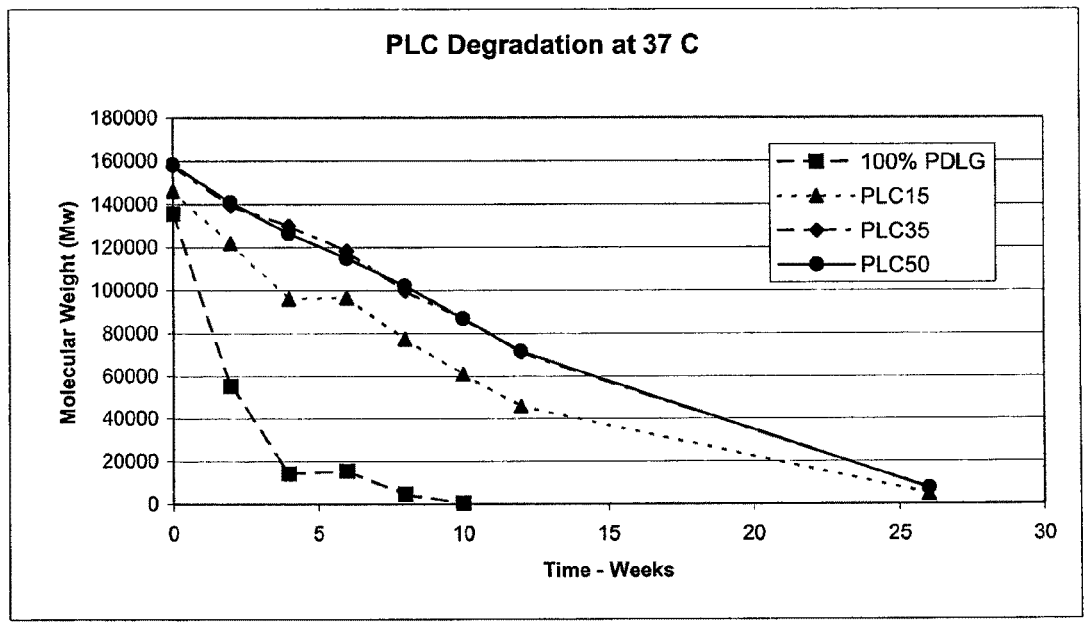

Figure 5. Mass Loss during real time degradation.
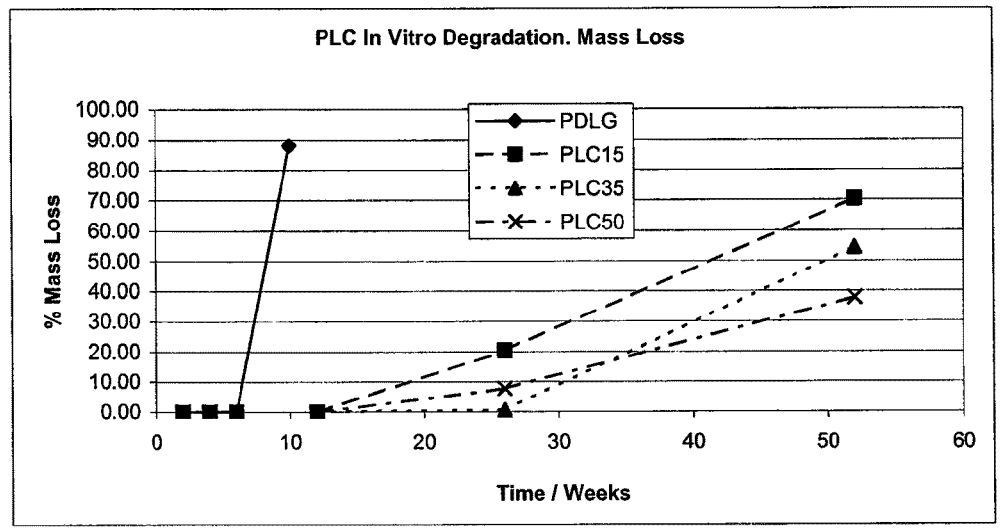
Figure 6. In Vitro Strength Retention.
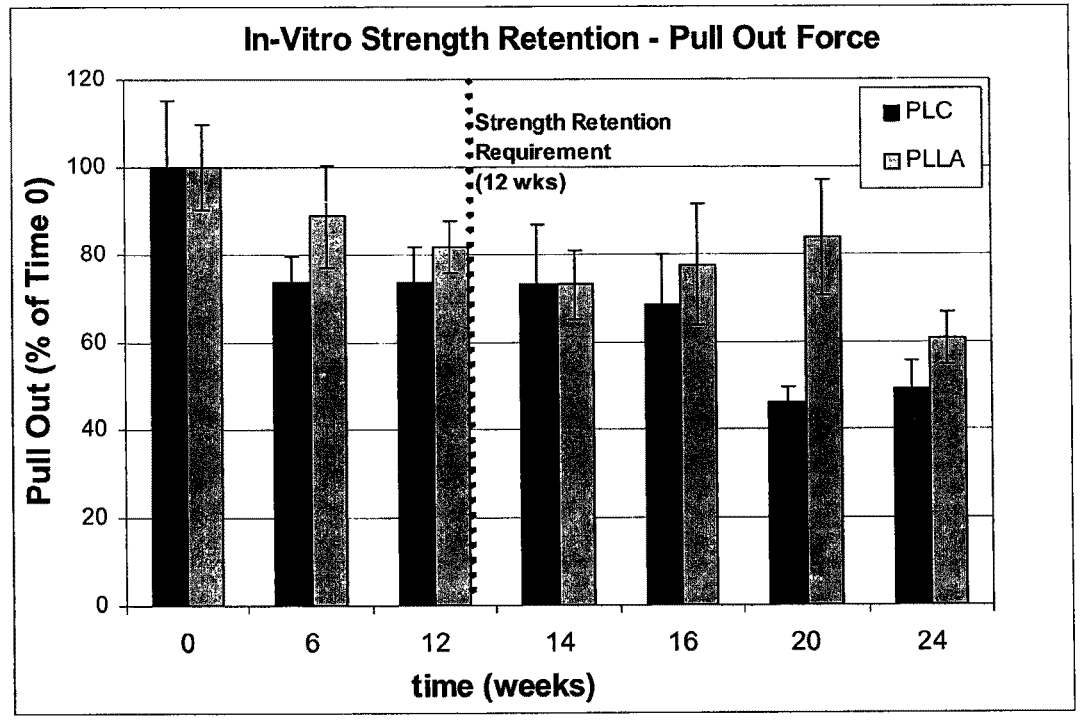

Averge mechanical strength at 12 week for the reconstructed ovine ACL.

CALAXO screw at 26 weeks. Stimulating of graft ossification by calcium release. Bone in-growth progressing through graft towards screw.

CALAXO screw site at 52 weeks. Bone in-growth progressed through graft towards screw. Full ossification within tunnel almost complete PLLA screw at 52 weeks. Screw not resorbed no bone integration within the tendon Z1- Above the screw approaching tibial plateau. Graft in tunnel.
Z2 – Above the screw mid tunnel. Graft in tunnel
Z3 – Screw region. Screw and graft in tunnel.

CALAXO screw. CT sections showing the progression of bone integration in both the graft and screw domains.

Figure 17a
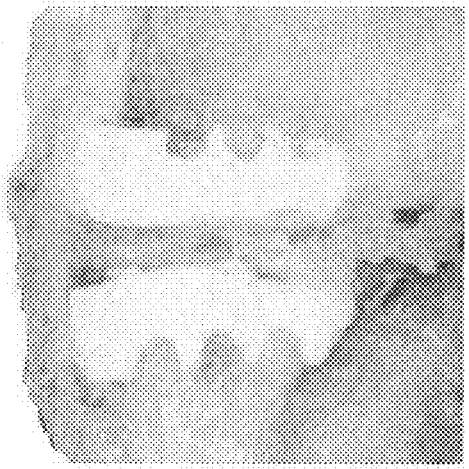
Figure 17b
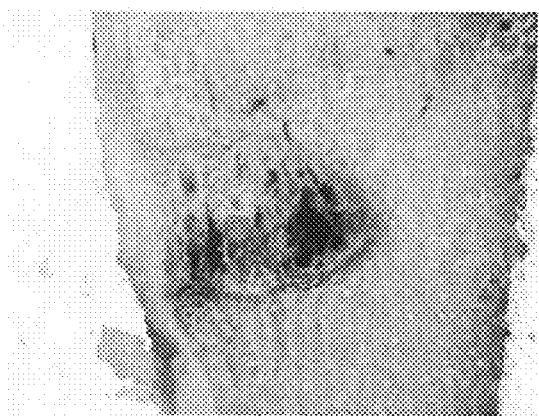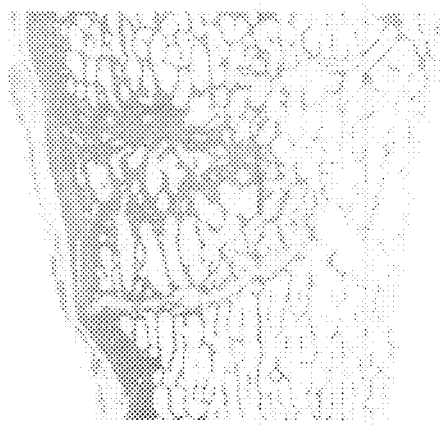
Figure 17c
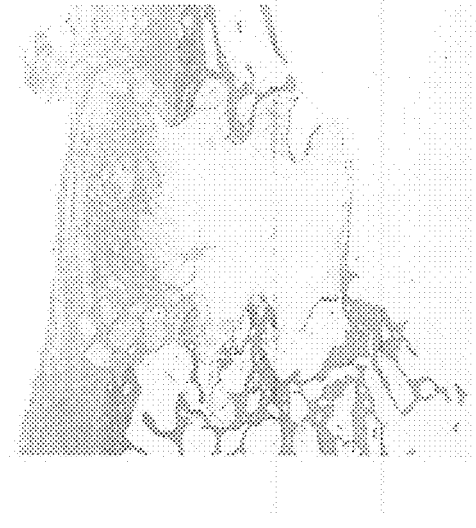

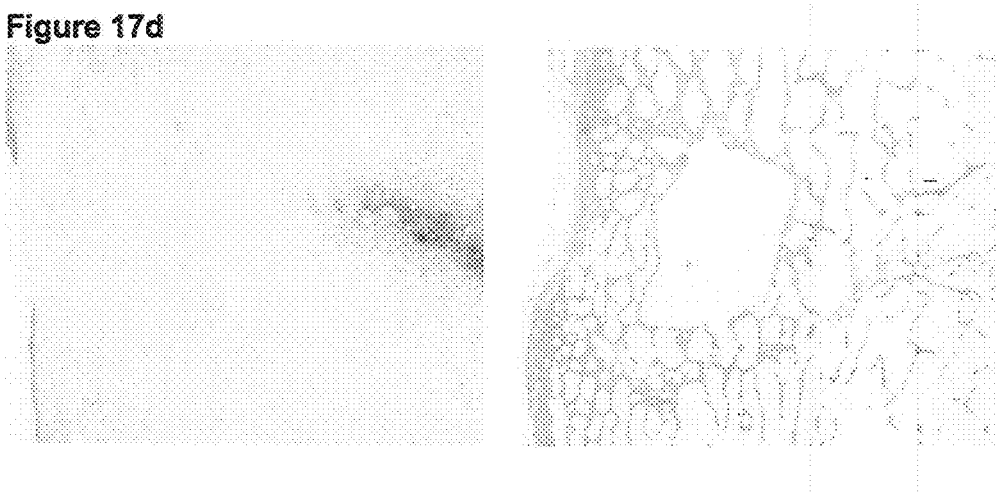

x3.2 magnification x25 magnification

BIOABSORBABLE POLYMERS

CROSS-REFERENCE TO RELATED APPLICATIONS

This application is a continuation-in-part of U.S. application Ser. No. 11/262,336, filed Oct. 28, 2005 now abandoned, which claims the benefit of U.S. provisional application No. 60/623,645, which was filed Oct. 29, 2004. The entire content of these prior applications is hereby incorporated by reference in the present application.

TECHNICAL FIELD

Described herein are compositions that include a biodegradable copolymer such as poly(lactide-co-glycolide) (PLGA), and methods of making and using devices containing such compositions.

BACKGROUND

Tissue fixation devices are used extensively to repair traumatic injuries, for example, those sustained during sporting events. Such "sports medicine fixation devices" are typically used to fix soft tissue and sometimes hard tissue back to bone. Sports medicine implants may be used to repair bone, chondral and/or osteochondral defects.

Bioabsorbable materials are used in both types of applications. For example, interference screws are used to fixate autologous grafts during anterior cruciate ligament (ACL) repair. The devices are often made from a semicrystalline polymer, poly(l-lactic acid) (PLLA) or copolymers of PLLA with poly(d,l-lactic) acid (PDLA) or poly(glycolic) acid (PGA). These bioabsorbable polymers produce acidic products upon degradation, and others have suggested inclusion of a buffering compound to neutralize the breakdown products (see, e.g., U.S. Pat. No. 6,741,329). Although appropriate for soft tissue repair, these materials can also be used in the event of orthopedic trauma or reconstructive surgery to fixate bone to bone.

The ideal bioabsorbable has sufficient mechanical properties to perform its primary function but over time the implant should ideally get replaced by natural tissue that is surrounding the implant. It certain embodiments the material releases compounds that aid the repair and replacement process.

SUMMARY

Described herein are biocompatible compositions that contain a copolymer and a filler material. For example, the compositions can include a copolymer that includes lactic acid and/or glycolic acid monomers and a filler such as calcium carbonate (e.g., about 30-40% $CaCO_3$ by weight (i.e., by weight of the composition as a whole).

In specific embodiments, the copolymer can be poly(lactide-co-glycolide) (PLGA), with a lactide:glycolide ratio of about 85:15 and the filler can be, for example, calcium carbonate or tricalcium phosphate. Alternatively, the copolymer can be poly l-lactide:d,l lactide (PLDL), with an l-lactide:d,l-lactide ratio of 70:30. We may refer to compositions containing calcium carbonate as Poly Lactide Carbonate or "PLC." The compositions described herein are also referred to herein as "materials" or "biomaterials" or, when the compositions are fashioned for a particular use, such as implantation, as "devices" or "implants." Further, where the devices are suitable for attaching one tissue to another (e.g., attaching soft tissue to bone or attaching bone to bone), we may refer to them as internal fixation devices. Such devices include screws, pins, rods, plates, sutures, suture anchors, staples, clips, rings, and the like. When fashioned to repair an injured bone (e.g., when used to replace lost bone fragments), the device can be described as a bone prosthesis.

The compositions described herein can be amorphous (i.e., they can be compositions in which the polymer chains are not ordered) or semi-crystalline (i.e., compositions in which there is some order to the polymer chains). On a macroscopic level, the compositions can have a pulverized or pelletized form (for example, the compositions described herein can be formulated as a powder or paste, or as pellets, granules, or interlocking shapes), or they can be shaped for use in a particular surgical procedure (for example, as a tissue fixation device or synthetic bone substitute or prosthesis). In any event, the compositions can be sterile. The compositions can also be fashioned as porous implants or devices. Methods for making such implants or devices are known in the art and can be carried out with the compositions described herein. For example, processes are known in the art for using porogens, leaching agents, supercritical $CO_2$, gas generating additives, and/or sintering techniques to fuse smaller shapes. The compositions described herein can also be molded into essentially any shape, whether regular (such as a cylinder or square) or irregular.

The compositions described herein are useful in a wide variety of methods in which tissue is altered, including methods in which the primary site of repair is bone per se. The methods encompass any type of tissue modification, including tissue repair, reconstruction, remodeling, and tissue-guided regeneration. In addition to their use as tissue fixation devices or synthetic bone substitutes or prostheses, the compositions described herein can be used as devices for attachment of orthopedic hardware (e.g., as screws for bone plates or screws to temporary secure hip stems) or in the context of reconstructive or cosmetic surgery.

In one embodiment, the composition may include a polymer formulation based on lactide and glycolide units that has a moderate degradation rate of 1-3 years. Into this polymer is blended both tricalcium phosphate (TCP) and calcium sulphate. The calcium sulphate will provide soluble calcium ions to aid repair. Local increases in calcium ions are known to increase bone formation which is critical in both getting the implant replaced by bone and to increase the tendon to bone repair. The TCP is a good osteoconductive agent and will enable longer term bone attachment and eventual replacement by bone.

In an alternative embodiment, the composition is biocompatible (i.e., substantially non-toxic) and includes a filler such as calcium carbonate, calcium sulphate, and/or tricalcium phosphate, and a copolymer formed from lactic acid monomers and/or glycolic acid monomers. The filler (e.g., calcium carbonate) can constitute more than 30% but less than 40% of the weight of the composition, regardless of the composition's form, the copolymer selected, or the inclusion of other components (e.g., a therapeutic agent, as described below). For example, the filler (e.g., calcium carbonate) can constitute more than 30% but less than about 34%; more than 30% but less than about 35%; or about 36% to less than 40% of the weight of the composition. The filler can constitute more than 30%; about 31%; about 32%; about 33%; about 34%; about 35%; about 36%; about 37%; about 38%; about 39%; or an amount therein between (e.g., an amount between 31 and 32%; an amount between 32 and 33%; and so forth). Where calcium carbonate is used, it can have the crystalline structure of calcite, and it may be present as calcium carbonate particles of a substantially uniform size (e.g., a majority of the calcium carbonate particles can be about 0.1-0.5; 0.5-2.5; 2.5-5.0; 5.0-7.5; or about 7.5-10.0/μm in size (size being measured across the particles' largest diameter)). Alternatively, the filler particles can vary in size (e.g., ranging in size in a uniform or non-uniform way from about 0.01/lm to about 10.0/μm).

Any of the fillers, including $CaCO_3$, can be combined with a PLGA copolymer in which the lactic acid monomers are in the L-form or the D-form, or are a mixture of the L- and D-forms. More specifically, the copolymer can be poly(dl-lactide-co-glycolide). The ratio of lactic acid and glycolic acid monomers within the polymer can also vary. For example, the copolymer can contain from about 50:50 lactide: glycolide units to about 90:10 lactide:glycolide units (e.g., about 85:15 lactide:glycolide units). It will be understood by one of ordinary skill in the art that these ratios can, and often do, vary due to manufacturing limitations. For example, the ratio can vary by about ±5%. Thus, it is to be understood that all references herein to the ratio of polymer units encompasses copolymers in which that ratio varies to an expected extent. In a specific embodiment, the composition includes (and may include only) a copolymer of lactide and glycolide units and more than 30% but less than 40% calcium carbonate by weight. In another specific embodiment, the composition includes (and may include only) poly(lactide-coglycolide) at 85:15 lactide:glycolide units and about 20-50% calcium carbonate by weight (e.g., about 20-30% (e.g., 25%), 30-40%, 40-50% (e.g., 45%), 30-34%, 35%, or 36-40%). Regardless of the precise components or their amounts, the copolymer can be amorphous or crystalline and the filler (e.g. $CaCO_3$) and the copolymer (e.g., PLGA) can form a substantially homogeneous mixture (e.g., the filler can be evenly or about evenly distributed within the copolymer; dispersed). Thus, the composition of any device, as a whole, fashioned from a substantially homogeneous mixture can also be homogeneous (e.g., the composition of a device at the proximal and distal ends of a screw or the opposite faces of a plate can be substantially indistinguishable in content).

The compositions described herein can, but do not necessarily, contain one or more additional components, which may be bioactive agents (e.g., therapeutic agents). For example, the compositions can contain a growth factor, including growth factors such as those from the fibroblast growth factor family, transforming growth factor family, or platelet derived growth factor family that act as chemoattractants and/or growth stimulators, a hormone such as human growth hormone, an antibiotic, an antiviral agent, an antifungal agent, an anti-inflammatory agent, an inflammatory mediator such as an interleukin, tumor necrosis factor, a prostaglandin, nitric oxide, an analgesic agent, an osteogenic factor such as a bone morphogenetic protein, or a matrix molecule such as hyaluronan. Other agents include angiogenic factors, which are capable of directly or indirectly promoting angiogenesis. Examples include angiogenic peptide growth factors in autologous, xenogenic, recombinant, or synthetic forms (e.g., a member of the vascular endothelial growth factor family). Further examples are blood clot breakdown products, such as thrombin and heparin including autologous, allogeneic, xenogeneic, recombinant and synthetic forms of these materials. Compositions based around butyric acid, including butyric acid (butanoic acid, $C_4H_8O_2$) and butyric acid salts, including sodium, potassium, calcium, ammonium and lithium salts, α-monobutyrin (1-glycerol butyrate; 1-(2,3 dihydroxypropyl) butanoate; $C_7H_{14}O_4$) and hydroxybutyrate can also be incorporated. Where the bioactive or therapeutic agent is a polypeptide, one can incorporate the polypeptide in its naturally occurring form or a fragment or other mutant thereof that retains sufficient biological activity to confer a benefit on the patient to whom it is administered. The polypeptides can be autologous in the sense that, where the recipient is a human patient, the polypeptide can have the sequence of a human polypeptide or a biologically active fragment or other mutant thereof. Alternatively, or in addition, the additional component can be a nutraceutical, such as a vitamin or mineral.

The bioactive material is included in an amount that is therapeutically effective for the organism (e.g., a human patient) in question. Inclusion of one or more bioactive materials may, for example, increase the rate of tissue repair, decrease the risk of infection, or otherwise aid the healing or post-operative process.

Also described herein are methods of making devices (e.g., internal fixation devices) with the compositions described herein. In one embodiment, the method can be carried out in steps that include the following: (a) providing a filler (e.g., calcium carbonate); (b) providing a copolymer (e.g., a copolymer formed from lactic acid monomers and glycolic acid monomers); (c) combining the filler and the copolymer to produce a composition in which the amount of the filler constitutes about 20-50% of the composition (e.g., more than 30% and less than 40% of the composition (e.g., about 35%); and (d) molding the composition to produce a device (e.g., an internal fixation device). In a specific embodiment, the method will produce a composition that includes (and may include only) a copolymer of lactide and glycolide units and more than 30% but less than 40% calcium carbonate by weight. In another specific embodiment, the method will produce a composition that includes (and may include only) poly(lactide-coglycolide) at 85:15 lactide and glycolide units and about 20-50% calcium carbonate by weight (e.g., about 20-30%, 30-40%, 40-50%, 30-34%, 35%, or 36-40%). The methods can further include a step of sterilizing the device by, for example, exposing it to radiation (e.g., gamma radiation), treating it with gases (e.g., chemical sterilization such as exposure to ethylene oxide gas), exposing it to heat (e.g., from steam, as in autoclaving), or exposing it to an electronic beam (e beam), or light (e.g., white light). Methods of sterilizing devices are known in the art, and one of ordinary skill in the art can select methods appropriate for a given device.

Optionally, the filler and copolymer can be combined with a bioactive agent (e.g., a therapeutic agent) including, but not limited to, any of those described herein. The therapeutic agent can be mixed or otherwise combined with the copolymer and filler or it can be added to the surface of the device or otherwise localized within the device.

If desired, one can omit the molding process of step (d). Thus, the methods described herein encompass those comprising steps (a)-(c) above, but not step (d). Therapeutic agents can also be included, and the composition can be sterilized and packaged, just as molded compositions can be sterilized and packaged.

The materials within the composition or device can be combined by any method that produces a satisfactory mixture that can be, if desired, formed into a shaped device. For example, a device can be formed by an extrusion process (e.g., a single screw, twin screw, disk, ram, or pulltrusion process); a molding process (e.g., an injection, intrusion, compression, or thermoforming process); a solvent based process (e.g., mixing or casting); a welding process (e.g., an ultrasonic or hermetic process); a polymerization process (e.g., reaction injection molding, bulk polymerization, and solvent polymerization); or by other methods (e.g., fiber spinning or electrospinning). The components within the compositions or devices can have the properties described herein.

For example, where the filler is calcium carbonate, it can have the particle size described above, the lactic acid monomers used can be in the D-form, L-form, or a mixture of D and L-forms, and so forth.

The compositions or devices can be packaged as kits, with instructions for further processing them or using (e.g., implanting) them. The instructions can be, but are not necessarily, printed instructions (e.g., the instructions can be supplied as an audio- or videotape or on a compact disc or similar medium). The kits can optionally contain materials suitable for processing or using the compositions or devices.

Also described herein are methods of using the compositions and devices to repair or remodel tissue. For example, the compositions and devices can be used in treating a patient who has sustained an injury in which a soft tissue within their body has become detached (wholly or partly) from bone. The methods can be carried out by using an internal fixation device as described herein (or made according to the methods described herein) to reattach the soft tissue to the bone. The soft tissue can be a ligament, (e.g., the ACL), a tendon, a muscle, cartilage, or other soft or connective tissue. In other embodiments, the compositions and devices described herein can be used to repair or reshape a bone or to attach bone to bone.

Also described herein are methods of treating a patient who has, or who is at risk for developing, osteomyelitis (an acute or chronic bone infection, usually caused by bacteria, and frequently associated with trauma, diabetes, and any condition associated with frequent disruption of the skin (e.g., hemodialysis, intravenous therapy, and drug abuse)). The method can be carried out by administering to the patient a composition or device described herein that includes an antibiotic. For example, where a patient has developed osteomyelitis in connection with a traumatic injury, the injury can be repaired with a suitable device that includes an antibiotic. Also described herein are methods of treating a patient who has bone cancer by administering to the patient (e.g., at the site from which a tumor has been excised) a composition comprising a composition or device described herein that includes a chemotherapeutic agent. For example, a patient having a bone cancer can be treated with a composition or device that includes any of the components described herein (e.g., poly(lactide-co-glycolide) and calcium carbonate) and a chemotherapeutic agent. As noted in connection with the compositions, the poly(lactide-co-glycolide) can include lactide:glycolide units at a ratio of 85:15, and the calcium carbonate can constitute about 20-50% of the composition by weight (e.g., more than 30% but less than 40% of the weight of the composition).

As copolymers such as PLGA degrade in vivo by hydrolysis into natural metabolic products, the compositions of the present invention and devices or implants made as described herein are biocompatible and may also be referred to as bioabsorbable (i.e., as able to degrade over time in a biological environment such as the human body to compounds that are removed during normal metabolic processes). Moreover, devices fashioned with the present compositions can degrade over a period of time that allows a desirable shift in weight bearing from the device to the patient's own tissues. While the compositions described herein are not limited to those having any particular advantage, we believe the inclusion of calcium carbonate decreases the rate of acid catalyzed hydrolysis, allowing for greater strength retention suitable for orthopedic repair devices. The release of calcium may stimulate bone cells and accelerate bone repair. The filler may also increase or enhance biocompatibility or dimensional stability, facilitate processing, and/or improve the appearance of the composition.

BRIEF DESCRIPTION OF THE DRAWINGS

FIG. 2a is a table depicting molecular weight loss for the compositions listed after 1, 2, and 4 days, as described in Example 1.

FIG. 2b is a line graph representing the tabular data of FIG. 2a.

FIG. 3 is a table indicating the pass/fail rating for four compositions (PDLG, PLCI5, PLC35, and PLC50) in a standard industry torsional test.

FIG. 4 is a line graph depicting the degradation of molecular weight for four compositions (PDLG, PLCI5, PLC35, and PLC50) over 26 weeks in vitro.

FIG. 5 is a line graph depicting the degradation of mass for four compositions (PDLG, PLCI5, PLC35, and PLC50) over 52 weeks in vitro.

FIG. 6 is a bar graph comparing the results of strength retention testing with PLC and PLLA over 24 weeks (as described in Example 3).

FIG. 17 shows histology from sheep implanted with screws made from poly 1 lactide-co-glycolide, calcium sulphate, β-tricalcium phosphate [PLG (85/15), $CaSO_4$, TCP 65:20:15], compared to empty defect controls. FIG. 17a shows representative fresh and stained sections from an implanted subject at 6 months post-surgery; FIG. 17b shows representative fresh and stained sections from an empty-defect control at 6 months post-surgery; FIG. 17c shows representative fresh and stained sections from an implanted subject at 12 months post-surgery; FIG. 17d shows representative fresh and stained sections from an empty-defect control at 12 months post-surgery.

DETAILED DESCRIPTION

Figure 1:
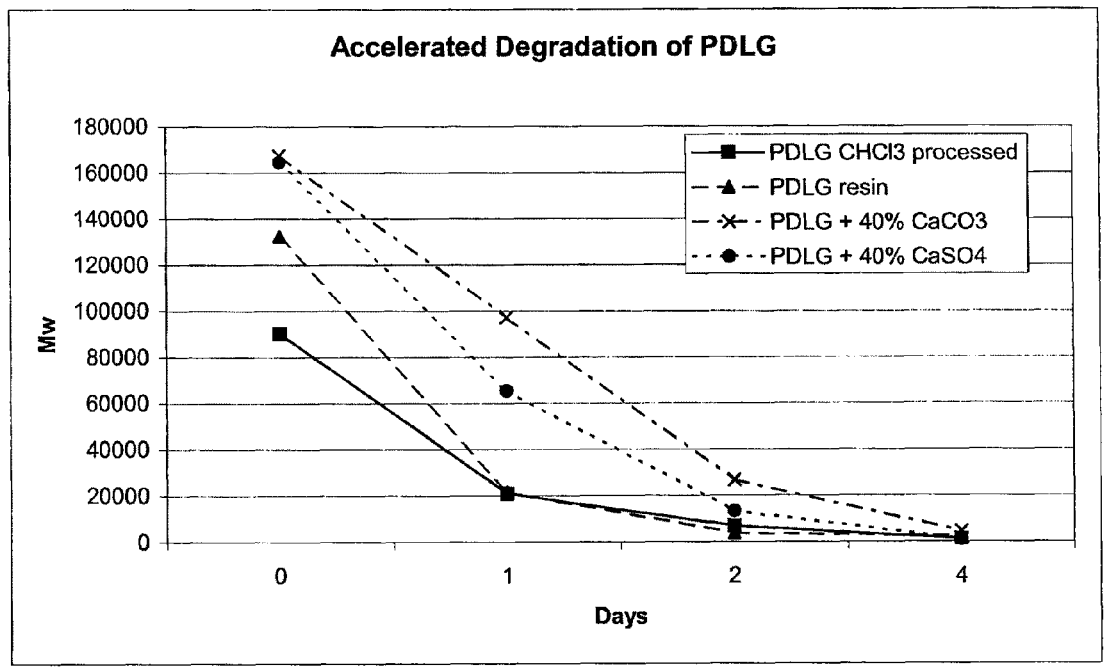
FIG. 1 is a table depicting % mass loss on days 1, 2, 4, and 5 from various compositions prepared as described in Example 1.

As noted, the compositions described herein can include a co-polymer and a filler material. These components, as well as additional components and methods of use are described further below.

Copolymers: As noted, the compositions described herein can include a copolymer, including copolymers produced from lactide and glycolide monomers. Lactide monomers can be present in the D-form or the L-form. Alternatively, the copolymer can include a combination of monomers in both the D- and L-forms (e.g., poly-l lactide:d,l lactide). For example, 20-28% of the lactide monomers (e.g., 25-75%, 30-70%, 40-60%, or about 50%) can be D-lactide monomers. As noted, where the co-polymer includes monomers of lactic and glycolic acids, we may refer to it as PLGA, and where both isoforms are present, we may refer to poly(dl-lactide-co-glycolide) (PDLGA). Moreover, the ratio of monomers (e.g., the ratio of lactide to glycolide units) can vary. For example, the copolymer can contain about 50:50 lactide:glycolide units to about 90:10 lactide:glycolide units (e.g., about 85:15 lactide:glycolide units; as noted above, the ratio can vary from these absolute numbers due to the manufacturing process). The copolymer can be manufactured by methods known to those of ordinary skill in the art or purchased from a commercial supplier.

Filler material: Materials suitable for inclusion as fillers with any of the copolymers described herein (e.g., with PLGA or PDLGA, for example where the ratio of lactide:glycolide units is about 85:15) include basic organic and inorganic metal compounds, such as acetates, lactates, glycolates, hydroxides, carbonates, phosphates, and halides. For example, the filler can be sodium acetate, potassium acetate, sodium lactate, potassium lactate, calcium lactate, potassium glycolate, calcium glycolate, calcium propionate, calcium oxide, calcium hydroxide, calcium carbonate, calcium phosphate family, calcium fluoride, calcium sulphate, magnesium oxide, magnesium hydroxide, magnesium carbonate, magnesium phosphate, sodium phosphate, sodium fluoride, potassium phosphate, potassium fluoride, or combinations thereof. A single filler such as calcium carbonate may be used as the sole filler or in combination with another filler material. Alternatively, combinations of two or more fillers can be used such as, for example, calcium sulphate and tricalcium phosphate. When a combination of fillers is used, the individual fillers may be, but need not be, present in equal amounts. For example, four parts calcium sulphate may be mixed with three parts tricalcium phosphate.

Like the copolymer, the filler material can be purchased from commercial suppliers or may be synthesized or purified from natural sources. For example, calcium carbonate is found in nature (e.g., in natural coral or other marine life). The filler may be pure or substantially pure, or it may contain contaminants. For example, the calcium carbonate may be pure or may contain small amounts (e.g., "trace" amounts) of another compound such as $MgCO_3$, $SiO_3$, or $[FeAl_2]O_3$. With respect to form, the calcium carbonate may be particulate, and the particles can be roughly spherical, cubical or tetrahedral measuring in size from very small (e.g., less than about 0.10 µm) to quite large (e.g., about 10.0 µm or more). For example, the particles can have a diameter of about 0.1-0.5 µm; about 0.5-2.5 µm; about 2.5-5.0 µm; about 5.0-7.5 µm; about 7.5-10.0 µm; or sizes within the ranges provided (e.g., about 8.0-9.0 µm). The particles, or a majority of the particles, can be of approximately the same size or they can be of a range of different sizes (e.g., the smallest can be about 0.01, 0.05, 0.10, 0.25, 0.50, 0.75, 1.0, 1.25, 1.50, 1.75, 2.00, or 2.50 µm and the largest can be about 5.0, 6.0, 7.0, 8.0, 9.0, or 10.0 µm). Regardless of size, the particles can be solid or can contain a hollow core, or can be porous in nature.

The amount of the filler within the composition can vary. For example, where the composition contains only a copolymer and filler, the filler can constitute about 20-50% of the composition (e.g., about 30-40% (e.g., about 35%)) by weight. For example, where the total weight of a composition is 100 g, it can include 60-70 g of a copolymer and 30-40 g of filler (e.g., 65 g of PLGA (e.g., PLGA at 85:15 lactide: glycolide units) and 35 g $CaCO_3$). Where one or more additives are included, as described below, the amount of the filler can nevertheless remain the same (i.e., about 20-50% (e.g., 30-40% (e.g., about 35%))) of the composition as a whole. Alternatively, the filler can constitute about 20-50% (e.g., 30-40% (e.g., about 35%)) by weight of the weight of the copolymer.

Additives: If desired, any of the compositions described herein (e.g., a mixture of PLGA (e.g., 85:15 lactide:glycolide units) and calcium carbonate), regardless of form, can contain one or more additives (e.g., therapeutic agents such as biotherapeutics or pharmaceuticals). For example, a calcium carbonate-PLGA composition (e.g., Poly Lactide Carbonate (PLC)) fashioned as a tissue fixation device or material for orthopedic application (e.g., a bone graft substitute) can include one or more additives (e.g., therapeutic agents). The additive(s) can be released as the device degrades or absorbs in vivo. Alternatively, or in addition, an additive can diffuse away from an intact device or can be positioned on the surface of the device so that it exerts an effect (e.g., an effect on surrounding tissue) after implantation. Accordingly, an additive may be incorporated throughout the device (e.g., it may form part of a substantially homogeneous device) or it may be spatially segregated (e.g., in an inner compartment or on the device's surface).

The therapeutic agent can be, or can include, a growth factor, including growth factors such as those from the fibroblast growth factor family, transforming growth factor family, or platelet derived growth factor family that act as chemoattractants and/or growth stimulators, a hormone such as human growth hormone, an antibiotic, an antiviral agent, an antifungal agent, an anti-inflammatory agent, an inflammatory mediator such as an interleukin, tumor necrosis factor, a prostaglandin, nitric oxide, an analgesic agent, an osteogenic factor such as a bone morphogenetic protein, or a matrix molecule such as hyaluronan. Other agents include angiogenic factors that are materials capable of directly or indirectly promoting angiogenesis. Examples include angiogenic peptide growth factors in autologous, xenogenic, recombinant, or synthetic forms (e.g., a member of the vascular endothelial growth factor family). Further examples are blood clot breakdown products, such as thrombin and heparin including autologous, allogeneic, xenogeneic, recombinant and synthetic forms of these materials. Compositions based around butyric acid, including butyric acid (butanoic acid, $C_4H_8O_2$) and butyric acid salts, including sodium, potassium, calcium, ammonium and lithium salts, a-monobutyrin (1-glycerol butyrate; 1-(2,3 dihydroxypropyl) butanoate; $C_7H_{14}O_4$) and hydroxybutyrate can also be incorporated. The therapeutic agent can also be a chemotherapeutic, cytotoxic, or immunotherapeutic agent. For example, the compositions can contain doxorubicin hydrochloride (Adriamycin), methotrexate with citrovorum, cisplatin, vincristine, cyclophosphamide, and/or dacarbazine.

Where antibiotics are incorporated, the compositions described herein can be used to treat osteomyelitis and may be administered prophylactically (e.g., in the event of bone surgery).

These therapeutic agents and other additives can be provided in physiologically acceptable carriers, including within sustained-release or timed-release formulations. Acceptable pharmaceutical carriers are well known in the art and are described, for example, in Remington's Pharmaceutical Sciences (Mac Publishing Co., A. R. Gennaro Ed.). Carriers are non-toxic to recipients at the dosages and concentrations employed, and include diluents, solubilizers, lubricants, suspending agents, encapsulating materials, solvents, thickeners, dispersants, buffers such as phosphate, citrate, acetate and other organic acid salts, anti-oxidants such as ascorbic acid, preservatives, low molecular weight peptides (e.g., peptides having less than about 10 residues) such as polyarginine, proteins such as serum albumin, gelatin or an immunoglobulin, hydrophilic polymers such as poly(vinylpyrrolindinone), amino acids such as glycine, glutamic acid, aspartic acid or arginine, monosaccharides, disaccharides, and other carbohydrates including cellulose or its derivatives, glucose, mannose or dextrines, chelating agents such as EDTA, sugar alcohols such as mannitol or sorbitol, counter-ions such as sodium, and/or non-ionic surfactants such as tween, pluronics, or polyethyleneglycol (PEG). Moreover, the additives can be linked to agents that facilitate their delivery. For example, an additive can be linked to an antibody or antigen-binding fragment thereof, including a single chain antibody, a growth factor, hormone, or other ligand that specifically binds a target (e.g., a cell surface receptor).

The substances within the compositions can be combined in any order. For example, the calcium carbonate and PLGA can be combined before the additive is introduced or all three types of ingredients (the filler, the copolymer, and the additive) can be combined at essentially the same time. The additive may be dissolved in a carrier (including those described above) and combined with a stabilizer or other agent (e.g., the targeting agents described above) before it is combined with another component.

The amount of additive incorporated into the composition can vary, but will be a therapeutically effective amount (i.e., an amount that confers a therapeutic benefit on the subject treated with the composition). To help preserve the composition, it can be packaged and stored under conditions in which the activity of the additive is likely to be preserved (e.g., ambient or cool temperatures (e.g., 4° C.)).

Therapeutically effective dosages may be determined by studies conducted in vitro or in viva Determining effective dosage levels (i.e., the dosage required to achieve a desired result) is well within the abilities of one of ordinary skill in the art. The position of the additive within the device and the rate at which it is released can also be varied to determine an optimal or acceptable rate of delivery. A typical additive dosage can range from about 0.001 mg/kg to about 1000 mg/kg, alternatively from about 0.01 mg/kg to about 100 mg/kg, or from about 0.10 mg/kg to about 20 mg/kg. The additives may be used alone or in combination with one another or with diagnostic agents.

Manufacturing: The filler material (e.g., calcium carbonate) and, optionally, an additive can be incorporated into the copolymer by any means known in the art (e.g., mixing, stirring, shaking, milling, melt blending or any other blending technique). Once incorporated, the combined materials can be formed into a device (e.g., a medical device, implant, or prosthesis, such as those described above). The device can be a tissue fixation device or it can be a material or device suitable for orthopedic application (e.g. the compositions described herein can be used as bone graft substitutes, spinal fusions, bone plates, bone plate screws, and the like). We may refer to bone substitute materials as "synthetic bone substitutes." The device can be fabricated by any method that involves a physical or phase change of the material or its components in order to form a specific resin, geometry, or product. For example, a device can be formed by an extrusion process (e.g., a single screw, twin screw, disk, ram, or pulltrusion process); a molding process (e.g., an injection, intrusion, compression, or thermoforming process); a solvent based process (e.g., mixing or casting); a welding process (e.g., an ultrasonic or hermetic process); a polymerization process (e.g., reaction injection molding, bulk polymerization, and solvent polymerization); or by other methods (e.g., fiber spinning or electrospinning). Pellets, powders, or other physical forms of the copolymer (e.g., pellets, granules, or interlocking shapes) can be coated with powders of the filler (e.g., calcium carbonate) with blending occurring in an extruder, which may be employed in the subsequent processing of the polymer to provide a useful medical device. Such devices include screws, pins, rods, plates, sutures, suture anchors, staples, clips, rings, and the like. In the case of a suture, the construction can produce a monofilament or multifilament suture (e.g., a braided, twisted, or spun suture made by conventional techniques such as those described in U.S. Pat. No. 5,019,093).

When intended for use as a synthetic bone substitute or an "infilling" item, the compositions can be fashioned into a paste-like product, which can be readily used to fill bone cavities or irregularities. The compositions described herein can be used as synthetic bone substitutes to treat injuries that result from trauma, surgery, or degenerative conditions that affect bone. Such substitutes provide an alternative to the use of autologous or allogeneic bone, and they can provide a matrix to facilitate bone growth and healing. We mention "infilling" above. The compositions described herein can be used to fill a donor site when an autologous bone graft is taken for use in another anatomical location. More specifically, the compositions described herein can be used in, or fashioned for use in, joint fusions, fracture treatment (e.g., fresh and non-union), revision hip procedures, and osteotomies.

In one embodiment, the filler (e.g., a $CaCO_3$ powder) can be added to a solution of the copolymer in an organic solvent, which is subsequently evaporated. Evaporation of the solvent (e.g., chloroform) can be facilitated by stirring or otherwise agitating the solution. Any residual solvent can then be removed in a vacuum oven. The sold mixture obtained may then be compression molded at a temperature at least equal to the softening temperature. The molded solid items can, if necessary or desired, be machined to a particular shape (e.g., the shape of a bone fragment they are meant to replace).

Compositions (e.g., amorphous compositions) and polymer-based devices used for medical purposes should also be sterile. Sterility may be readily accomplished by conventional methods such as irradiation or treatment with gases or heat, an electronic beam (e beam), or light (e.g., white light). For example, the polymer-based compositions described herein can be sterilized through steam sterilization (e.g., by autoclaving), treatment with ethylene oxide (EtO) gas, or exposure to radiation (e.g., γ irradiation) (see, e.g., Athanasiou et al., *Biomaterials* 17:93-102, 1996; Baker et al., J. Biomed. Mat. Res. 46:573-581, 1999; Besong et al., *J. Bone Joint Surg.* 80-B:340-344, 1998; Buchanan et al., *Biomaterials* 20:823-837, 1999; Costa et al., *Biomaterials* 19:659-668, 1998; Dillow et al., *Proc. Natl. Acad. Sci. USA* 96:10344-10348, 1999; Gogolewski and Mainil-Varlet, *Biomaterials* 17:523-528, 1996; Gogolewski and Mainil-Varlet, *Biomaterials* 18:251-255, 1997; Kurtz et al., *J. Biomed. Mat. Res.* 46:112-120, 1999; Kurtz et al., *Biomaterials* 20:1659-1688, 1999; Pascaud et al., *Biomaterials* 18:727-735, 1997; Ratner et al., Eds., *Biomaterials Science: An Introduction to Materials in Medicine*, Academic Press, pp. 415-420, 1996; and Sauer et al., *Biomaterials* 17:1929-1935, 1996).

Steam sterilization is a common form of sterilization that sterilizes materials by exposing them to high temperature steam (over about 121° C.), under pressure (about, or more than, two atmospheres), for about 15-30 minutes. As autoclaving can harm polymeric biomaterials, an alternate method of sterilization may be used. As noted, the compositions described herein can also be sterilized by exposure to EtO gas, which kills microorganisms by alkylating the amine groups on nucleic acids. To prevent or reduce toxicity (EtO can attack the same amine groups in humans that it attacks in microorganisms), materials sterilized with EtO can be washed (e.g., washed 2-10 times with air) (Kurtz et al., *Biomaterials* 20:1659-1688, 1999 and Ratner et al., Eds., supra). Radiation (e.g., γ radiation) sterilizes materials by ionizing the nuclei acids of any contaminating microorganisms. A typical application is of 60Co at 25-40 kGy). If required, more detailed procedures for sterilizing materials by these methods are readily available, and one of ordinary skill in the art is easily able to perform them. Accordingly, the methods of manufacturing a polymer-based composition (e.g., a PLGA/$CaCO_3$ containing composition) can include the step of sterilizing the composition.

Regardless of the precise method by which the compositions are sterilized, the goal is to remove (or destroy or disable) living organisms (e.g., bacteria) or other disease-causing agents (e.g., viruses, fungi, yeast, molds, and prions) from (or within) the composition. Sterility is generally quantified using the sterility assurance limit (SAL) and process conditions determined by performing fractional sterilization runs. The SAL is the probability that a given implant will remain nonsterile following a sterilization run, and the accepted minimum value for the SAL is 10-6. At that value, one implant in one million may be nonsterile.

Use: The compositions and devices can be used in a wide variety of situations to treat patients who have experienced an injury (exemplary tissue fixation devices and materials for orthopedic application are described above). While human patients are clearly candidates for treatment, the invention is not so limited. Veterinary application is also possible (the animals may be domesticated pets (such as dogs or cats), farm animals (e.g., horses, cows, goats, pigs, or sheep), laboratory animals (such as rodents or non-human primates), or wild animals (e.g., a nonhuman primate or other mammal (e.g., an animal kept in a zoo>>. The compositions can also be used in the event of elective surgery, including cosmetic surgery. The method may be one in which soft tissue is attached to bone or one in which the primary site of repair is bone per se. The process can encompass any type of tissue modification, including tissue repair, reconstruction, remodeling, and tissue-guided regeneration, including wholly internal processes as well as processes that include or affect the skin or an orifice such as the mouth or nose (e.g., the compositions described herein can be used in dental procedures).

EXAMPLES

Example 1

Poly-dl-lactide-co-glycolide (PDLG) (85:15) with $CaCO_3$ or $CaSO_4$

The studies described here were designed to evaluate the hypothesis that basic fillers such as calcium carbonate and calcium sulfate delay the degradation rate of amorphous polymers, including PDLG having about 85% lactide units and 15% glycolide units. We used dried PDLG 85:15 with an initial intrinsic viscosity (I.V.) of 1.16. The calcium carbonate and calcium sulfate had a purity of over 99%.

To mix the copolymer and filler, we began by dissolving various components in a solvent. Each of the following were dissolved in 150 ml chloroform: (1) 15 g of PDLG; (2) 9 g of PDLG and 6 g of calcium carbonate; and (3) 9 g of PDLG and 6 g of calcium sulphate. The materials were allowed to dissolve in the solvent over several hours. The solutions were agitated periodically and then emptied out onto a glass tray. As the solvent evaporated, a thin film of mixed polymer and filler formed on the tray. The film was peeled off the tray and compression molded as described below. PDLG resin was also compression molded directly.

To compression mold the materials, we preheated a compression molder to 150° C. We placed the mold onto the lower mold plate, and filled the cavity with approximately 15 grams of material before inserting it into the compression molder. The material sat for approximately five minutes or until the polymer resin began to adhere to itself. We then increased the heat to approximately 180° C. and let the material sit until a consistent melt had formed. The top mold plate was placed onto the bottom mold plate, and the mold clamp was screwed down to compress the sample. After 10 seconds, we released the pressure to allow gases to escape, then reapplied the pressure and let sample cure for 30-60 seconds. The mold was removed, quenched under cold water, and opened using a rubber mallet. We used a band saw to cut the disc into parts (0.5"×0.75"), which were placed in 100 ml of a buffer solution at 67° C. Samples were removed from the solution at time zero and after 1, 2, 4, 7, or 9 days, and dried to constant weight at 50° C. under vacuum. Mass loss was recorded before the samples were subjected to GPC analysis. Their thickness was also measured before and after degradation.

The percentage mass loss is shown through day five in the table of FIG. 1, and the loss of molecular weight is presented in tabular and graphical form in FIGS. 2*a* and 2*b*, respectively. The results clearly demonstrate that the degradation of poly dl lactide co-glycolide is retarded by the addition of calcium sulphate and calcium carbonate. This can be seen in both the molecular weight loss and the mass loss of the polymer. Calcium carbonate was more effective in slowing the degradation rate than calcium sulphate.

Example 2

Degradation Studies of Molded Implants

The purpose of this study was to evaluate poly(dl-lactide-co-glycolide (85:15)) (PDLG) blended with calcium carbonate, as a material for bioabsorbable medical devices, specifically interference screws. We evaluated in vitro degradation characteristics to determine the effect of calcium carbonate on the rate of degradation of these polymers in a molded form and assessed the materials for initial torsional strength.

The pure polymer was molded following drying using a standard molding procedure into an interference fixation screw. We produced filled material by blending calcium carbonate into PDLG. The weight of the filler, as a percentage of the polymer, was 15, 35, or 50%. The resulting material is designated poly lactide carbonate (PLC); materials containing 15% calcium carbonate are designated PLC15; those containing 35% are designated PCL35; and those containing 50% are designated PLC50. The materials were molded according to standard molding procedures into an interference fixation screw and tested for torsional strength. A pass/fail criteria based on industry specifications was used to determine if the materials had sufficient torsional strength to be used as interference screws.

For in vitro degradation testing, each screw was placed in phosphate buffered saline (PBS) and maintained at a temperature of 37° C. The incubated samples were assessed for molecular weight, and for mass loss, at 0, 2, 4, 6, 8, 10, 12, 26, and 52 weeks. The molecular weight of the degraded samples was analyzed using chloroform GPC and compared with the starting material to evaluate degradation during in vitro conditioning.

The torsional test results shown in FIG. 3 indicate that that PDLG and PLC15 and PLC35 have acceptable torsional strength. PLC50 failed this test indicating that the filler level is too high and this material is not well suited for bio-medical screw applications.

The loss in molecular weights, depicted in FIG. 4, clearly shows the effect of calcium carbonate on the degradation rate. The rate is slowed down by addition of calcium carbonate. This is proportional to the mass ratio of the calcium carbonate in the PLC until 35% is reached. No difference could be seen between PLC35 (35% calcium carbonate) and PLC50 (50% calcium carbonate). Mass loss data (shown in FIG. 5) also clearly demonstrates the effect of calcium carbonate on PDLG. Samples of PDLG showed considerable mass loss (88%) after 10 weeks in vitro. For samples of PLC15, mass loss began between 12 and 26 weeks in vitro, as 20% mass loss was realized at 26 weeks. No significant mass loss was shown at 26 weeks for samples of PLC35, and PLC50. Samples of all three PLC blends showed significant mass loss at 52 weeks (70%, 54%, and 30%, for PLC15, PLC35, and PLC50, respectively). An ASH test was performed on the degraded materials and, assuming no mass loss was attributed to calcium carbonate, the materials had all lost nearly 90% of their polymer portion. Our conclusions from this study are as follows: (1) the degradation rate of poly(dl lactide-co-glycolide) is too fast for fixation device applications that require strength retention to 12 weeks; (2) the addition of calcium carbonate decreases the rate of degradation in proportion to the amount of calcium carbonate in the polymer until around 35-40% by weight; (3) Initial torsion testing indicated torsion strength for this design device is below acceptable levels for the composition with 50% calcium carbonate. Based on these studies, we considered further analysis of PLC with about 35% calcium carbonate. This formulation contained enough calcium carbonate to slow the degradation rate and thereby enhance strength retention, but not so much calcium carbonate that the initial mechanical properties of the compositions were compromised.

Example 3

Further Degradation Studies (Strength Retention)

This study was designed to evaluate the in vitro mechanical characteristics of a sterilized tibial fixation screw (7×9×25 mm) produced from Poly Lactide Carbonate (PLC); poly-dl lactide-coglycolide (85:15) blended with calcium carbonate 65:35 w/w. We evaluated the material for strength retention characteristics and used poly-l-lactide (PLLA) tibial fixation screws as controls.

To test strength retention, we cut saw bone (20 pct) into cubes (4×4×4 cm) and drilled an 11 mm hole through the center of each cube. We then cut leather straps (25.5×1.5 cm) from standard 1.5 mm thick leather (natural vegetable KIP, grade A), folded it in half, and inserted it through the hole to form a loop coming out the other side of the cube. We took care to position the leather within the hole to ensure the strap followed the circumference of the hole, forming a channel in the center of the strap. The screw was then inserted down this channel until the head of the screw was just below the surface of the saw bone.

We placed each saw bone block containing a screw and leather strap into a 500 ml sealed jar filled with PBS, and placed the jar in a water bath at 37° C. Samples were removed one day, 6, 12, 14, 16, 20, 24 weeks later for mechanical testing. For both the experimental (PLC) screw and the control (PLLA) screw, ten replicates were performed at each time point.

The samples were tested to failure by placing the bone block under a standard Instron base grip. The loop of the leather was attached to a hook fixed to the load cell of the Instron and pulled to failure at 1 mm/second. The results are shown in FIG. 6. No significant difference (p=0.01) was seen between the two materials at any of the three time points to 12 weeks. Therefore, mechanical pull-out testing has shown that screws made from PLC retain fixation strength comparable to that of screws made from PLLA for at least 12 weeks.

Example 4

Evaluation of a Tapered Screw in an Ovine Model

PLC and PLLA screws were implanted directly into the cancellous bone of the left medial distal femur of an ovine model. Histology and computed tomography (CT) were performed over time to assess biocompatibility and bone integration into the screws.

Figure 7:
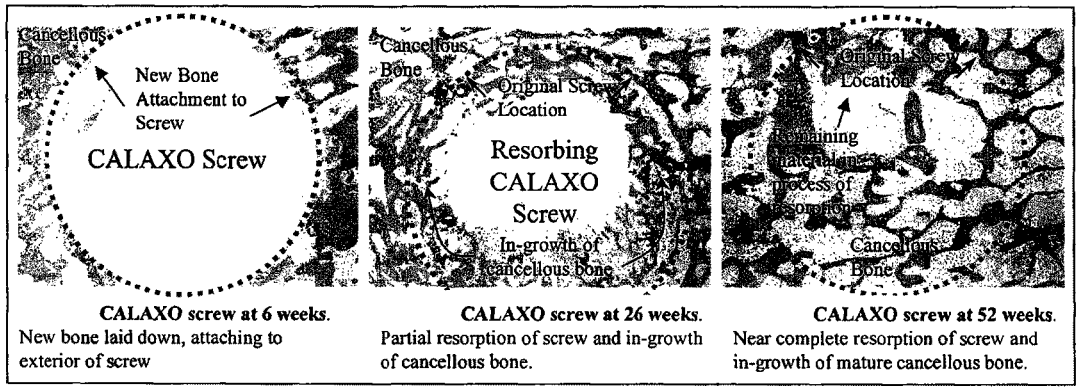
FIG. 7 is a series of three photographs of an implanted PLC screw at six weeks, 26 weeks, and 52 weeks (left to right) following implantation into the femur of a sheep.
Figure 8:
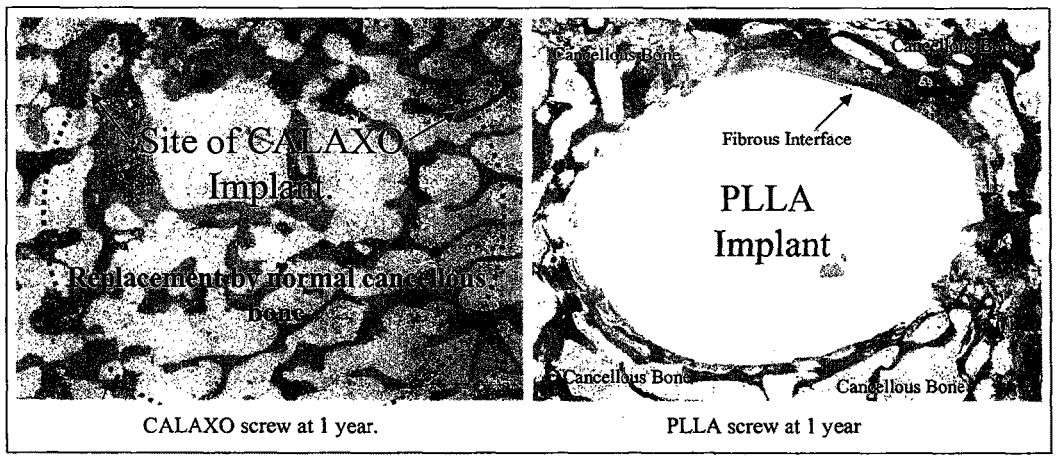
FIG. 8 is a pair of photographs of an implanted PLC screw (left-hand photograph) and a PLLA screw (right-hand photograph) one year following implantation into the femur of a sheep.

The histological analysis performed on the PLC screw revealed new bone formation at all time points examined, starting with new bone formation and attachment around the margin of the screw at six and 12 weeks (FIG. 7, left-hand photograph). At 26 weeks the PLC screw was partially integrated with bone (FIG. 7, center photograph), and at 52 weeks, the screw was replaced with new bone (FIG. 7, right-hand photograph). In contrast, the PLLA screw was still present and surrounded by fibrous tissue even after 52 weeks implantation. These results indicate that the PLC screw is osteoconductive. The amount of bone formation increased with time in the group of animals that received the PLC screw, as the screw degraded and was replaced by cancellous bone. At one year, the implant site was fully healed with normal cancellous bone. Even after this extended period of time, the PLLA screw was fully present; there was no sign of resorption (FIG. 8). These results are consistent with our prior studies demonstrating that PLLA degrades extremely slowly and is not replaced by bone.

Figure 9:
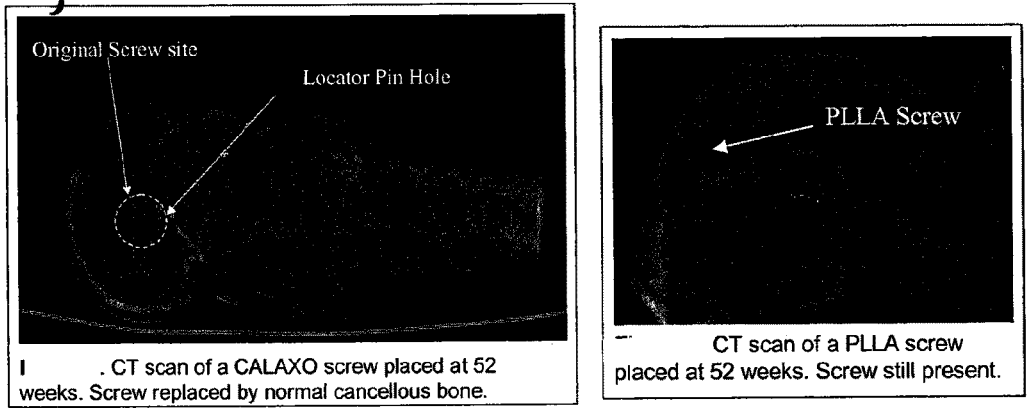
FIG. 9 is a pair of CT scans. The left-hand scan shows the location of a PLC screw in the femur of a sheep after 52 weeks implantation (the screw was replaced by normal cancellous bone). The right-hand scan shows a PLLA screw after the same period of time. The PLLA screw is still present.

Computed tomography results for the PLC screw showed extensive bone integration at 26 weeks and new bone formation by 52 weeks. The new bone formation was so extensive that no evidence of the screw could be seen. These results support our belief that the PLC screw is osteoconductive. The PLLA screw was still present at 52 weeks in all animals tested (see FIG. 9).

Figure 10:
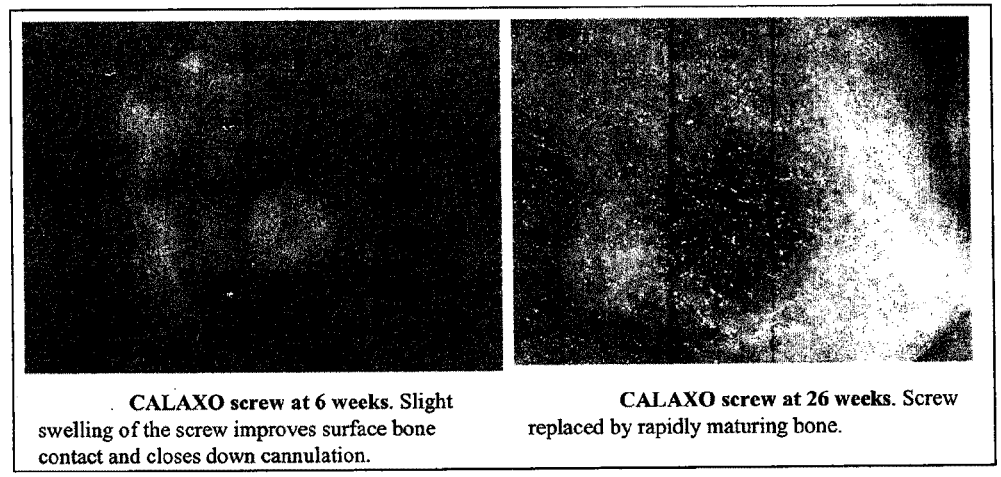
FIG. 10 is a pair of photographs of the sites of implantation of a PLC screw six weeks after implantation (left-hand photograph) and 26 weeks after implantation (right hand photograph).

Macroscopically, the PLC screws were easily seen at 6 and 12 weeks following implantation. It was difficult to identify the PLC screw after 26 weeks, and it was not possible after 52 weeks due to the extent of bone integration. We believe the slight swelling of the PLC screw improves surface-bone contact and closes down cannulation (see FIG. 10, left-hand photograph). After 26 weeks, the PLC screw was in the process of being replaced by rapidly maturing bone (see FIG. 10, right-hand photograph).

Based on this study, we concluded that: (1) when placed directly in cancellous bone, the PLC screw was gradually replaced with normal bone and is, therefore, osteoconductive; (2) PLLA screws remain present in cancellous bone for at least 52 weeks; (3) the PLC material is biocompatible (bone attachment was seen at the earliest time point studied); and (4) the combination of an amorphous bioabsorbable polymer and calcium carbonate is ideal for use in devices such as sports medicine fixation devices.

Example 5

In Vivo ACL Study

Figure 11:
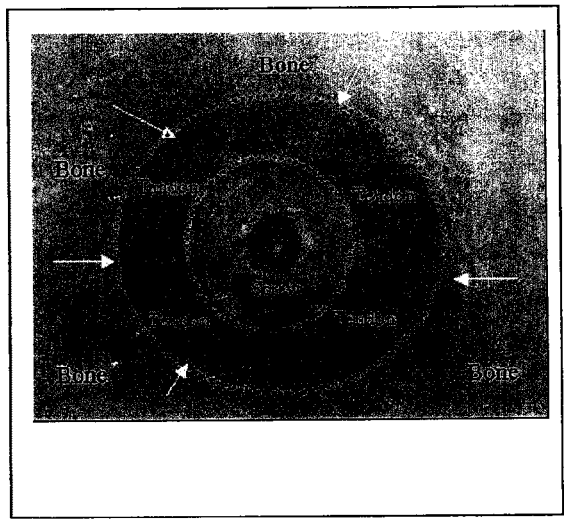
FIG. 11 is a photograph illustrating central placement of a screw completely surrounded by a tendon graft.

A PLC screw was compared to a PLLA interference screw in a soft tissue ACL model. The screws were placed in the center of a four-stranded graft, which represents the worst-case scenario for bone integration, as the screw is fully encapsulated with tendon tissue (see FIG. 11). This model is unlike many fixation techniques, where the screw is placed alongside the graft and in contact with bone that will enhance bone integration.

Mechanical testing was performed to assess overall repair strength and failure modes to 12 weeks (n=10). This time point was chosen because it is well established that graft/tunnel healing and fixation occurs in approximately four weeks using bone-tendon-bone (BTB) grafts and before 12 weeks using soft tissue grafts in ACL repair (Grana et al., *Am. J. Sports Med.* 22:344-351, 1994; Rodeo et al., *J Bone Joint Surg.* 75-A:17951803, 1993; Weiler et al., *Arthroscopy* 0.18:113-123, 2002).

Histology and CT were used to assess biocompatibility, tendon-bone integration and bone formation. These tests were performed at 6, 12, 26, and 52 weeks following implantation, with six replicates at each time point.

Figure 12:
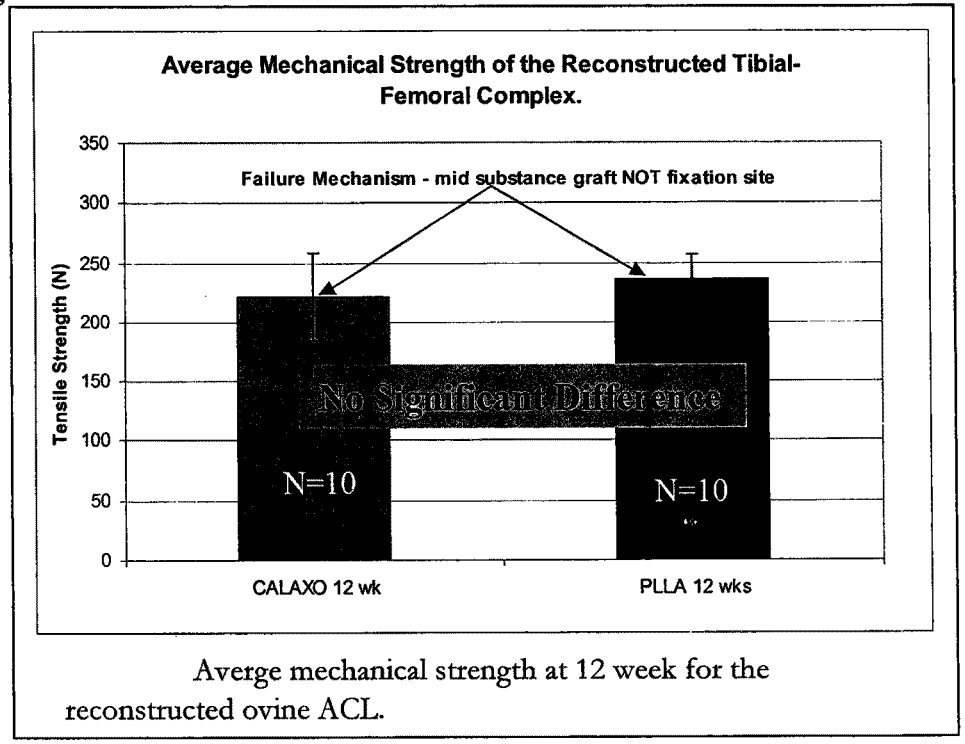
FIG. 12 is a bar graph comparing the tensile strength (N) in the reconstructed tibial-femoral complex in animals treated with PLC screws and animals treated with PLLA screws.

We did not observe any difference in mechanical properties of the repaired ACL in animals treated with the PLC screw and animals treated with the PLLA interference screws (the results obtained at 12 weeks are shown in the graph of FIG. 12).

Figure 13:
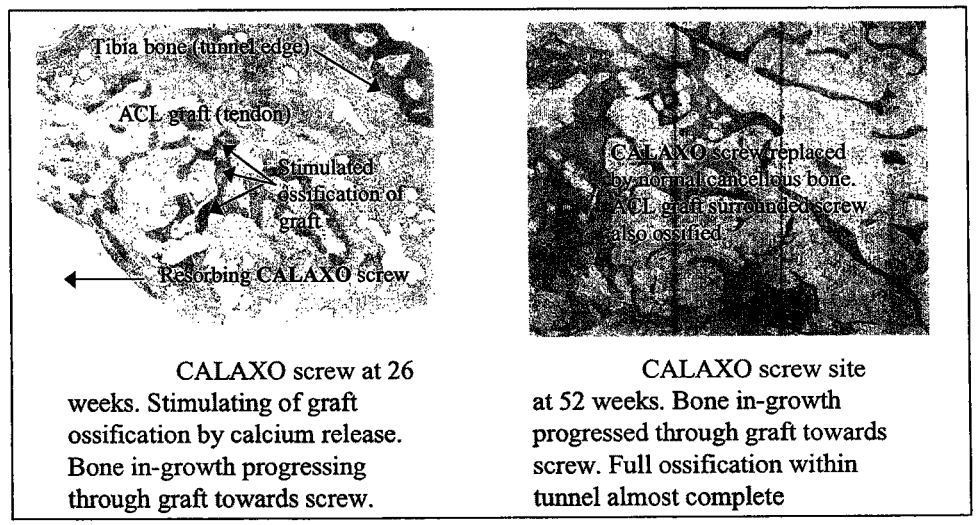
FIG. 13 is a pair of photographs illustrating the ability of a PLC screw to stimulate graft ossification (presumably by calcium release) after 26 weeks implantation (left-hand photograph) and after 52 weeks implantation (right-hand photograph).
Figure 14:
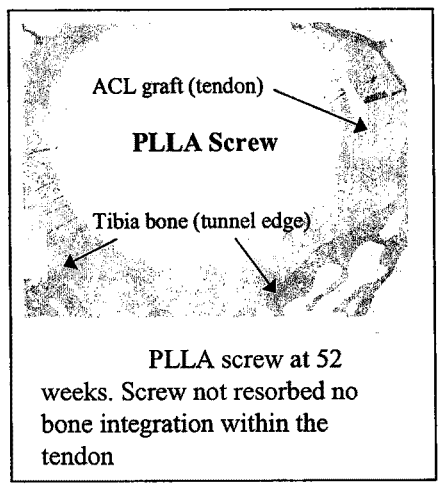
FIG. 14 is a photograph illustrating a PLLA screw after 52 weeks implantation under the same conditions as the PLC screw shown in FIG. 13 (and described in Example 5).

Our histological analysis demonstrated that, within one year, the PLC screw was replaced by bone, and the material also stimulated bone formation in the tendon graft within the tunnel. FIG. 13 illustrates the stimulating effect the PLC screw has on the surrounding graft tissue. Ossification of the graft can clearly be seen in the tunnel containing the PLC screw, but no ossification was seen around the PLLA screw. Ossification was stimulated in the PLC-repaired graft by 26 weeks and both the PLC screw and the surrounding ACL graft were ossified by 52 weeks (FIG. 13). New bone formation was noted within the tendon graft in only the PLC-treated group. The PLLA screw remained intact and inert at 52 weeks (FIG. 14).

The PLC screw also stimulated the ossification of the tendon graft away from the screw position but still within the tunnel. This ossification was not seen in animals treated with the PLLA screw (FIG. 14). Thus, our histological analyses support the hypotheses that the PLC screw is replaced by bone when placed in an osseous site; is an osteoconductive material; and actively stimulates ossification of the tendon graft within the bone tunnel.

Figure 15:
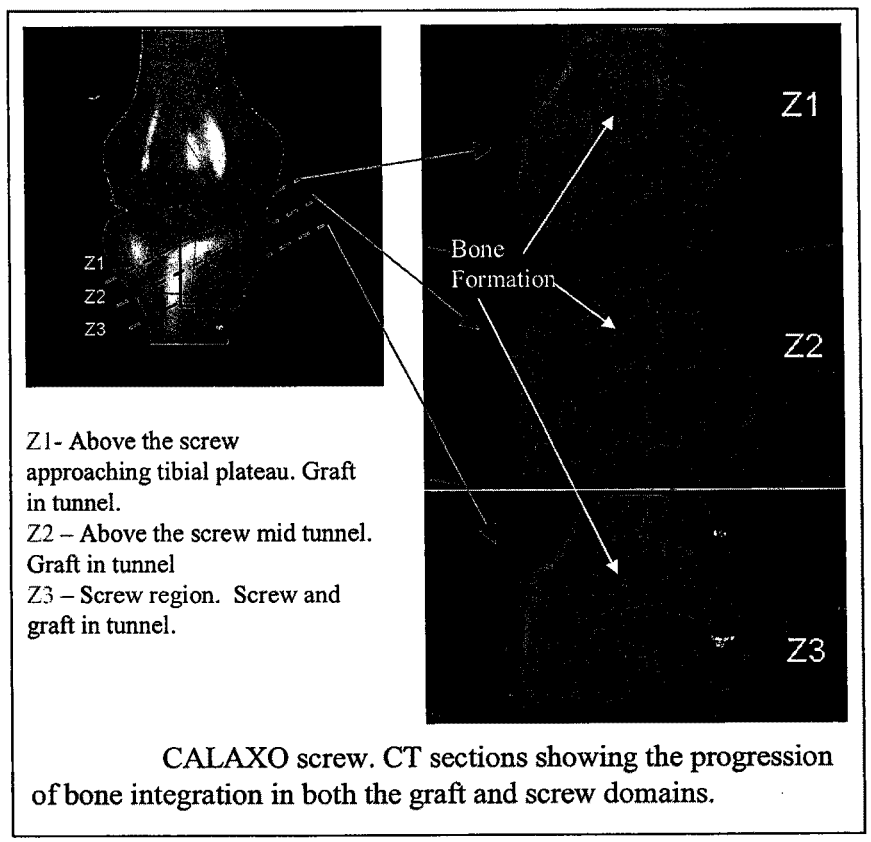
FIG. 15 is a series of CT sections through the planes shown as Z1, Z2, and Z3, showing the progression of bone integration in both the graft and PLC screw domains.

CT was performed to examine bone formation with the bone tunnel for both the PCL and PLLA screws. The PLLA screws were present at all time points examined with no demonstrable in vivo resorption. The PLC screws were replaced by bone and bone formation was noted throughout the tunnel within the graft indicating the bone stimulating effect of PLC. CT sections in three planes, showing the progression of bone integration in both the graft and screw domains are shown in FIG. 15.

These studies support the following conclusions: (1) PLC screws are biocompatible and exhibit fixation strength equivalent to the PLLA screws (both providing adequate mechanical fixation until healing had occurred); (2) the PLC material was osteoconductive, facilitating in-growth of bone into the implant material; and (3) the PLC screws actively stimulated bone formation with a tendon graft that was present in the bone tunnel. Further, the intra-articular portion of the graft, articular cartilage and synovium was normal throughout the study for both PLC-treated and PLLA-treated animals. Thus, the PLC screws are useful as a healing material and may be ideal for use in interference screws used for ACL reconstruction.

Example 6

In Vivo ACL Study

The formulation, broadly classified as a composite, is composed of a polymer and ceramic filler. Two polymers, poly l-lactide-co-glycolide 85:15 (PLG) and poly l-lactide:d,l-lactide 70:30 (PLDL), were separately blended into the same percentage of ceramics. The ceramic portion of the formulation is composed of two different ratios of tricalcium phosphate (TCP) and calcium sulphate.

Within the total formulation, the polymer is at a loading level of 65% and the ceramics are at a loading level of 35%. One formulation has 65% poly l lactide:co-glycolide 85:15, 20% calcium sulphate, and 15% tricalcium phosphate. The other formulation is composed of 65% poly l-lactide:d,l-lactide 70:30, 20% calcium sulphate, and 15% tricalcium phosphate (note: all percentages are weight-percentages).

Example 7

In Vitro Degradation Study the Comparing Suture Anchors Made from the Formulation of Poly l Lactide-Co-Glycolide, Calcium Sulphate, Tricalcium Phosphate [PLG (85/15), CaSO4, TCP 65:20:15] with a Commercialized Suture Anchor, the LUPINE BR To evaluate the fixation strength, molecular weight and mass loss during in vitro degradation of poly l lactide-coglycolide, calcium sulphate, tricalcium phosphate [PLG (85/15), CaSO4, TCP 65:20:15] also called the Osteoraptor 2.3, and Lupine BR instability suture anchors (control) at 37° C.

Each anchor was inserted into the prepared holes of a polyurethane block using the appropriate instrumentation and technique recommended for respective suture anchor. Each bone block with inserted anchor and was placed in a plastic jar and filled with phosphate buffered saline. The jar was then be placed in an oven at 37° C. and samples removed at the following time points of 0, 6, 12, 18, 26 weeks for mechanical testing. The Osteoraptor suture anchor was additionally tested at the following time points, 2, 4, 8, 10, 14, 16, 20, 24 weeks. The sample number was nine. The suture anchors was mechanically evaluated on the electromechanical testing machine and the molecular weight will also be determined at each time point.

Figure 16:
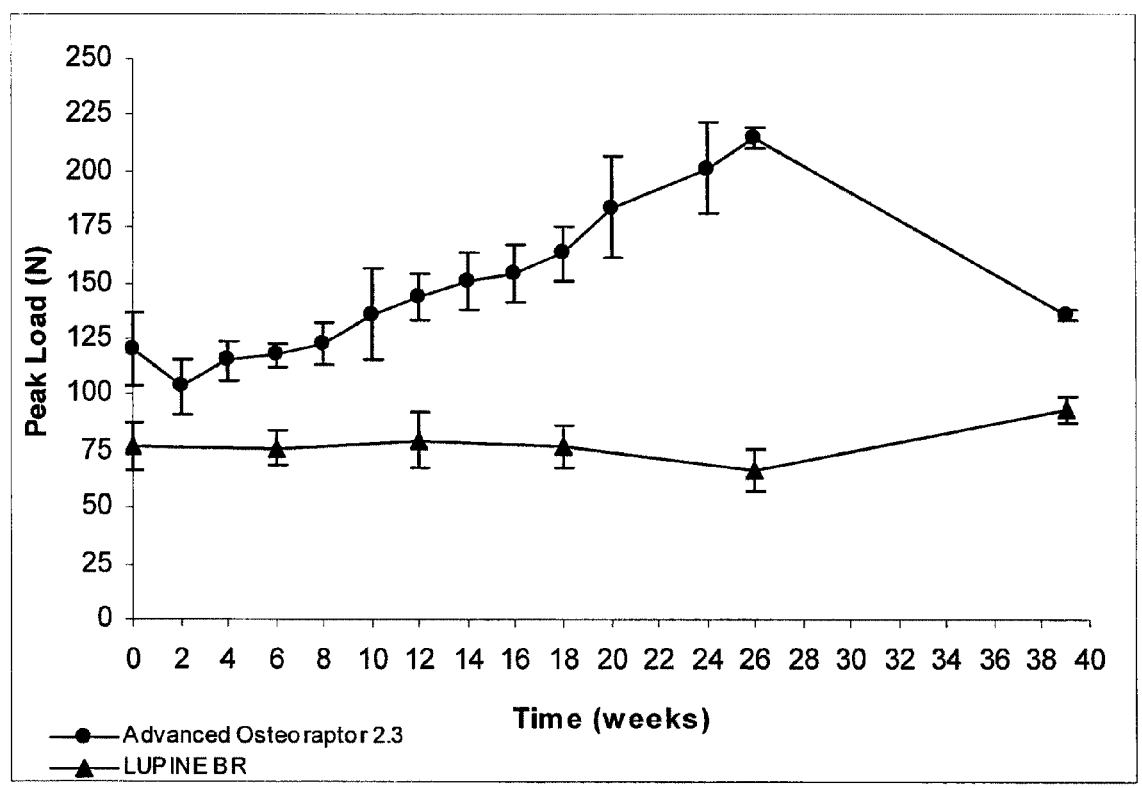
FIG. 16 shows peak load for the Osteoraptor 2.3 and Lupine BR suture anchor during in vitro degradation.

The peak load of the suture anchors was evaluated over twenty-six weeks. Results showed that within twenty-six weeks the fixation strength of the Osteoraptor 2.3 suture anchor increased 79%. It was shown that the twenty-six week results were significantly greater (p-value<0.05) than baseline results. At thirty-nine weeks the peak load decreased, but was statistically equivalent (p-value=0.940) to baseline results. The results were analyzed by a two student t-test with 95% confidence intervals. The Lupine BR suture anchor was stable from baseline to eighteen weeks with a slight decline by week twenty-six and an increase at thirty-nine weeks. (Error! Reference source not found. FIG. 16)

The molecular weight of the Osteoraptor 2.3 and Lupine BR suture anchor was also evaluated over fifty-two weeks. It was shown that the initial weight average molecular weight of the Advanced Osteoraptor 2.3 suture anchor was lower than the Lupine BR suture anchor. However, between six and twelve weeks similar values were reached. The values continued to decline, when the formal mechanical evaluation ceased, through twenty-six weeks and at thirty-nine weeks. At fifty-two weeks the overall Osteoraptor 23 suture anchor weight average molecular weight loss was 93.3%, while the Lupine BR loss was 97.6%.

Example 8

Summary of the Histological Evaluation of Specimens from Resorbable Screw Study 6, 12 and 18-Month Post-Implantation The objective of this animal study was to evaluate a new bioresorbable material molded into screws compared to empty defect in an ovine direct-in-bone model. An empty defect control was used as to demonstrate the critical size nature of the defect in this model. Screws (9×10 mm) were manufactured to the out of the formulation of poly l lactide-co-glycolide, calcium sulphate, β-tricalcium phosphate [PLG (85/15), CaSO$_4$, TCP 65:20:15].

The ovine direct-in-bone model is bilateral; each leg received an implant in the distal medial femur and proximal medal tibia for a total of 4 implantation sites per animal. An 8.5×9 mm defect was created in each site and either filled with a 9×10 mm implant or left empty. Implants were left 1 mm proud to the surrounding bone. A 1.5 mm fully threaded, self-tapping cortical screw was inserted approximately 1-1.5 cm caudal to each implant to mark placement for histological preparation. Each time point sample size was 6 animals. Twenty-four adult Merino whethers underwent surgery without complication and with adequate pain management.

All animals survived until their respective time points were reached. They were sacrificed at 6, 12, and 18 months and were noted to have unremarkable necropsies. Samples were collected and were processed for histological analysis.

Histology Summary

6 Months

The screws were intact and had retained their shape. Surface has an uneven appearance and may be due to slight expansion of the screws. Bone was visible penetrating into the thread of the screw and in contact with the surface. Minimal fibrous tissue is evident at the screw/bone interface. Minimal cellular reaction to the screws was noted. Empty defects were all noted to have new bone growth, with bridging across the gap at the cortical surface.

12 Months

The majority of the implants were highly fragmented. Ceramic particles were evident. There was evidence of bone growth into the threads of most of the specimens. In the empty group, two of the defects had entered the medullary cavity and in the remaining specimens repair had not progressed. Although new bone growth was evident at the cortical surface, large spaces filled with marrow were noted deeper in the defect.

18 Months

The majority of the screws were degraded and what remained was highly fragmented. In areas of the defect the fragments had become enveloped by new bone growth. New bone growth tended to occur at the periphery of the defect whereas at the surface, and extending deeper into the central aspect of the defect, fibrous tissue was evident. Empty defects were difficult to identify in tibial sites, but voids in femoral sites were noted in a few samples.

Histomorphometry analysis noted that there was an increase in new bone growth surrounding the screw, which was still present at 6 months. At this time, this new bone growth around the screw averaged about 14.3%. The empty defect averaged at 18.5% new bone growth. At 12 months, new bone surrounding the screw material as it started to degrade averaged about 16%. At 18 months, bone in-growth into the defect site was noted with about 24.3% new bone formation, which is nearly a 2-fold increase from the 6 month data. The empty defects tended not to heal.

Conclusions.

PLG (85/15), CaSO$_4$, TCP 65:20:15 bioabsorbable screws when placed in bone degraded slowly over an 18 month time period. By the 18 month time point the defect, where the implant had been present, was slowly being ingrown with bone.

Example 9

In Vivo Study Summary: Evaluation of a New Suture Anchor in an Ovine Patellar Tendon Reattachment Model The objective of this animal study was to evaluate a new bioresorbable material molded into suture anchors and compare to results from a previous study. Suture anchors were manufactured to the 2.3 mm BIORAPTOR design out of poly-L-lactide-co-glycolide, calcium sulphate, and tricalcium phosphate (PLG/CS/TCP). The control group used from the previous study was composed of Poly-L-lactide (PLLA).

The ovine patellar-tendon reattachment model utilizes an external fixator to immobilize the stifle (knee) joint of the sheep over a 3-week period relieving a reattached major extensor tendon, the patellar tendon, time to heal and regain adequate strength. Once the fixator was placed, each of 10 sheep had surgery that sharply dissected the patellar tendon and reattached it to the decorticated tibial tuberosity utilizing two anchors. There were 5 sheep in each material group. All sheep survived the surgery without complication for the 3-week period while in fixators. The animals had no surgery-related complications up to the 12 week time point.

Figure 18:
FIG. 18: 40× representative image of PLG/CS/TCP anchor interphase with bone. A thin layer of fibrous tissue containing scant macrophages is present, indicating a mild foreign-body response with no reactivity tissue/implant nor tissue/bone.
Figure 19:
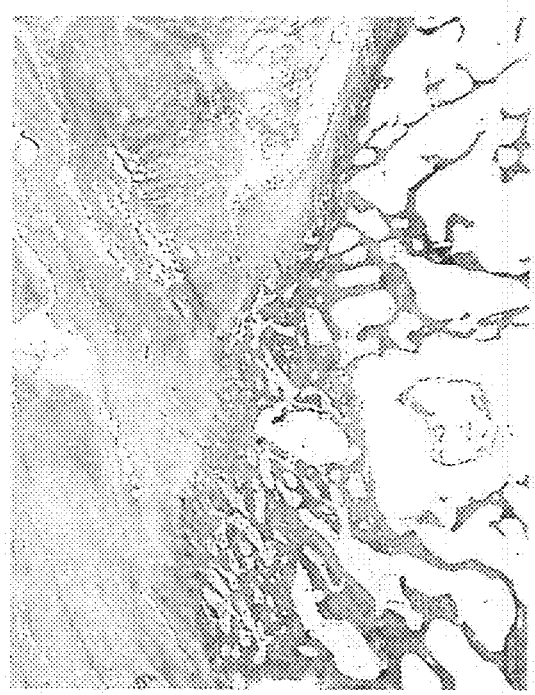
FIG. 19: 3.2× image show a representative section from the PLG/CS/TCP group.
Figure 20:
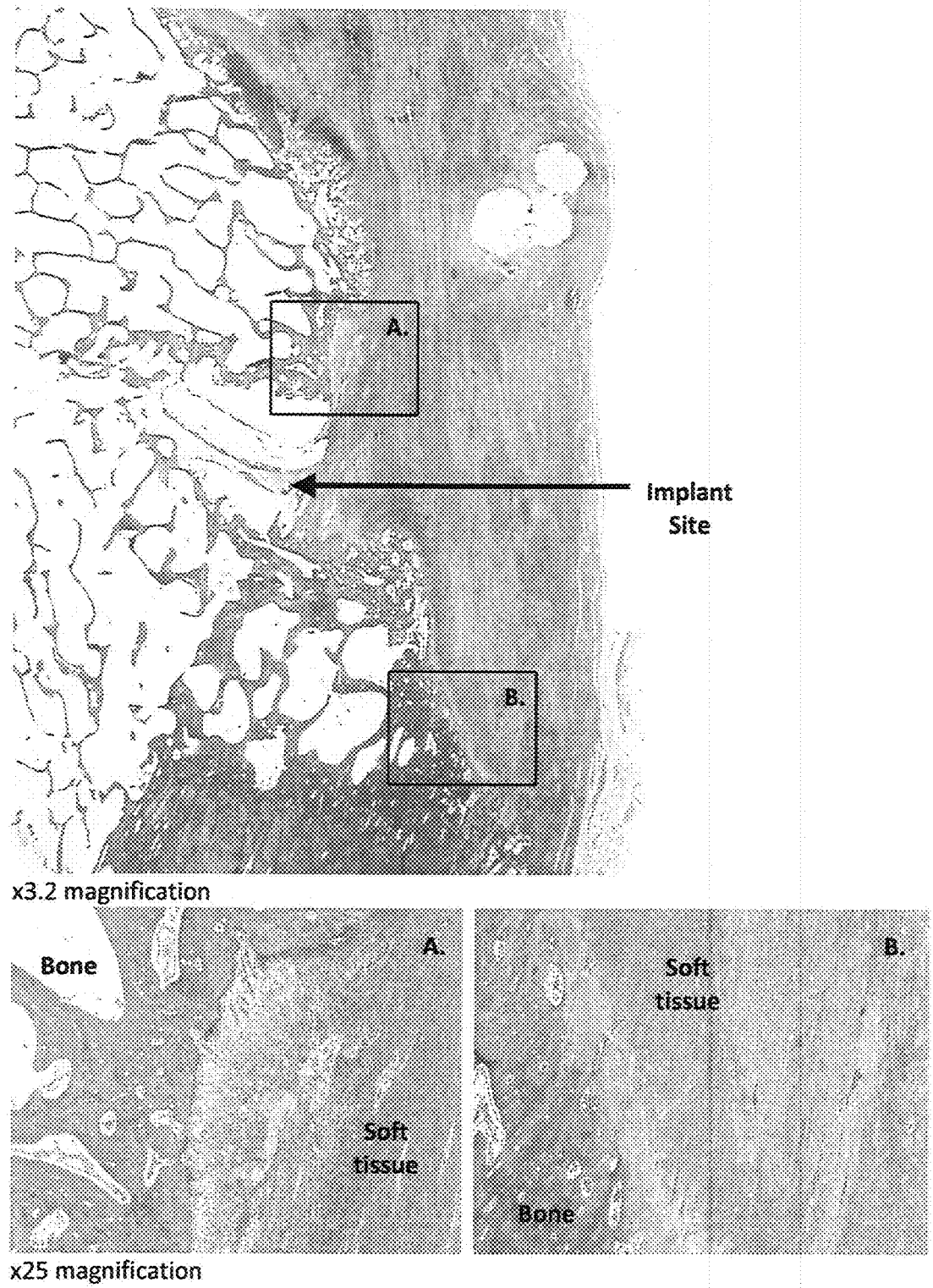
FIG. 20: Representative histology of the Bioraptor (PLLA) anchor implantation site at 12 weeks post-surgery. Panels A and B represent higher magnification photomicrographs of the areas designated in the large upper panel. In each panel the areas of bone and soft tissue are as denoted.
Figure 21:
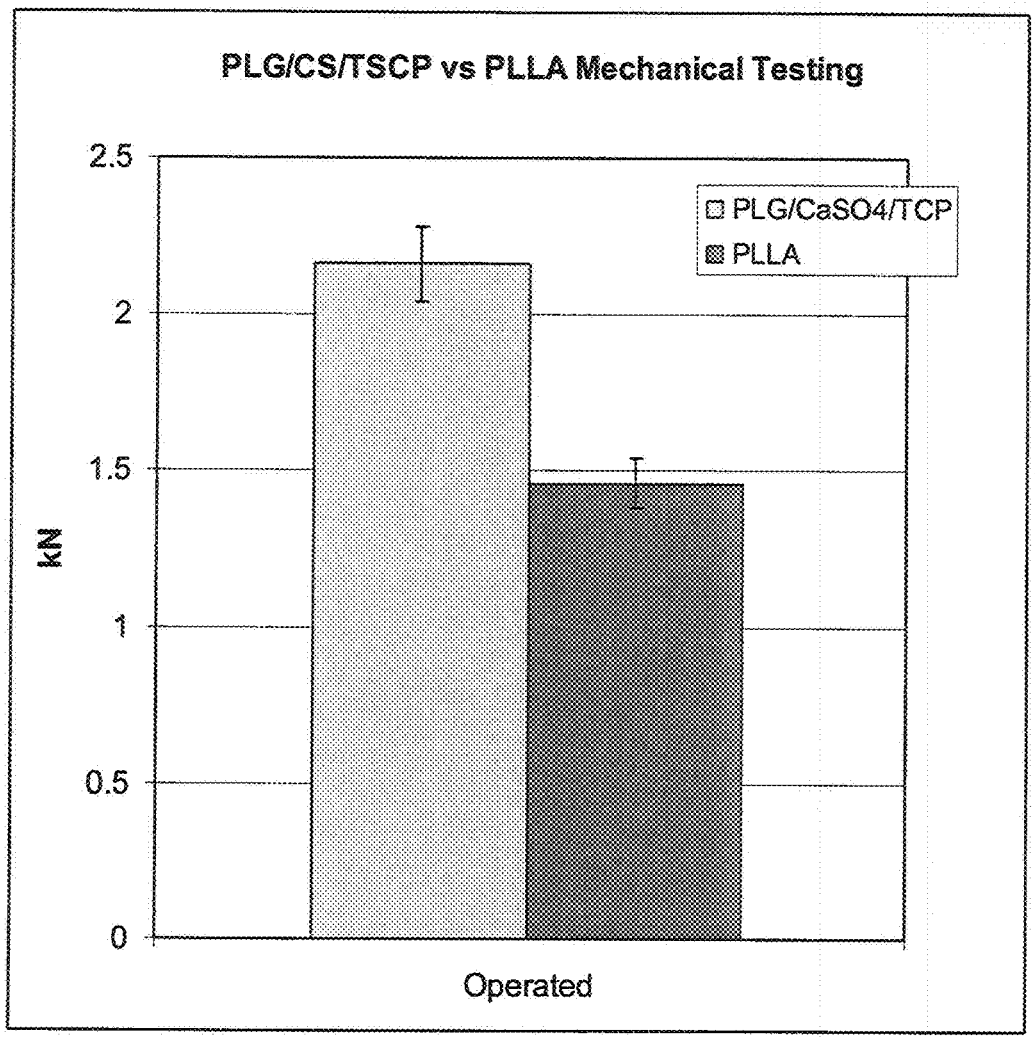
FIG. 21: Comparison of failure strengths using historical control data (PLLA) and current study data (PLG/CS/TCP).

Animals at time of sacrifice were noted to have unremarkable necropsies. Common findings for groups were small patello-femoral lesions from the K-wire penetrating the joint. No evidence of arthritic change was present in this joint, the femorotibial joint, or the patellar tendon enthesis grossly. Four animals were noted to have a minor reduction in range-of-motion. Histology was performed on mechanically tested samples (FIGS. 18-20). Tissue reactions showed minimal reactivity. Mechanically, the PLG/CS/TCP had higher failure strengths to the historical control from the previous study. Repairs using PLG/CS/TCP anchors in fact had significantly higher failure strength than those made of PLLA (FIG. 21).

CONCLUSION

A new material was assessed in a patellar reattachment model in sheep and evaluated using histology and biomechanical testing. Overall, these materials showed they produced minimal reactivity histologically. The new material had higher failure strength overall compared to a previous study with the control material as repairs completed with PLG/CS/TCP anchors were significantly stronger compared to repairs with PLLA anchors.

What is claimed is:

1. A fixation device comprising a polymer and a ceramic filler, wherein the polymer is about 65% and the ceramic filler is about 35%;
    the polymer comprises poly(dl-lactide-co-glycolide) wherein the poly(dl-lactide-co-glycolide) is about 85:15;
    and the ceramic filler comprises calcium carbonate.

2. The fixation device according to claim 1, wherein the filler comprises material purified from natural sources.

3. The fixation device according to claim 1, wherein the filler comprises synthetic material.

4. The fixation device according to claim 1, wherein the filler comprises a mixture of synthetic material and material purified from natural sources.

5. A method comprising a step of securing soft tissue to a bone using the fixation device of claim 1.

6. The method of claim 5, wherein the soft tissue is a ligament, tendon, muscle, or cartilage.

7. The method of claim 6, wherein the tendon is the patellar tendon, quadriceps tendon, semitendonosus tendon, gracilis tendon, or a combination thereof.

8. The method of claim 5, wherein the bone is the patella.

9. The method of claim 5, wherein the ceramic filler of the fixation device comprises material purified from natural sources.

10. The method according to claim 5, wherein the ceramic filler of the fixation device comprises synthetic material.

11. The method according to claim 5, wherein the ceramic filler of the anchor comprises a mixture of synthetic material and material purified from natural sources.

12. The method according to claim 5, wherein the fixation device is an interference fixation screw.

13. A fixation device comprising a polymer and a ceramic filler, wherein the polymer is about 65% and the ceramic filler is about 35%;
    the polymer comprises poly(l-lactide-co-glycolide) wherein the poly(l-lactide-co-glycolide) is about 85:15; and
    the ceramic filler comprises calcium sulphate and tricalcium phosphate wherein the calcium sulphate:tricalcium phosphate is about 20:15.

14. The fixation device according to claim 13, wherein the filler comprises material purified from natural sources.

15. The fixation device according to claim 13, wherein the filler comprises synthetic material.

16. The fixation device according to claim 13, wherein the filler comprises a mixture of synthetic material and material purified from natural sources.

17. A method comprising a step of securing soft tissue to a bone using the fixation device of claim 13.

18. The method of claim 17, wherein the soft tissue is a ligament, tendon, muscle, or cartilage.

19. The method of claim 18, wherein the tendon is the patellar tendon, quadriceps tendon, semitendonosus tendon, gracilis tendon, or a combination thereof.

20. The method of claim 17, wherein the bone is the patella.

21. The method of claim 17, wherein the ceramic filler of the fixation device comprises material purified from natural sources.

22. The method according to claim 17, wherein the ceramic filler of the fixation device comprises synthetic material.

23. The method according to claim 17, wherein the ceramic filler of the anchor comprises a mixture of synthetic material and material purified from natural sources.

24. The method according to claim 17, wherein the fixation device is an interference fixation screw.

* * * * *